United States Patent
Yamada et al.

(10) Patent No.: US 7,424,827 B2
(45) Date of Patent: Sep. 16, 2008

(54) INSPECTING METHOD OF ELASTIC BODY, INSPECTING APPARATUS THEREOF, AND DIMENSION PREDICTING PROGRAM THEREOF

(75) Inventors: Tomohiro Yamada, Nagoya (JP); Masato Komazawa, Nagoya (JP); Tetsuya Hatta, Nagoya (JP); Takatoshi Nehagi, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 146 days.

(21) Appl. No.: 11/115,981

(22) Filed: Apr. 27, 2005

(65) Prior Publication Data

US 2005/0284224 A1 Dec. 29, 2005

(30) Foreign Application Priority Data

| Apr. 27, 2004 | (JP) | ............................. 2004-131376 |
| Aug. 31, 2004 | (JP) | ............................. 2004-253310 |
| Feb. 28, 2005 | (JP) | ............................. 2005-055022 |

(51) Int. Cl.
*G01N 29/036* (2006.01)

(52) U.S. Cl. ............................. 73/579; 73/582; 73/602; 73/862.59

(58) Field of Classification Search .................... 73/649, 73/862.59, 702, 517 AV, 704, 504.12, 504.02, 73/504.03, 504.14, 514.34, 579, 582, 597, 73/602, 717

See application file for complete search history.

(56) References Cited

U.S. PATENT DOCUMENTS

| 5,165,289 A | * | 11/1992 | Tilmans ..................... 73/862.59 |
| 5,566,573 A | * | 10/1996 | Yost ............................. 73/643 |
| 5,777,228 A | | 7/1998 | Tsuboi et al. |
| 5,821,424 A | * | 10/1998 | Rodriguez ..................... 73/657 |
| 6,186,004 B1 | * | 2/2001 | Kaduchak et al. ............. 73/596 |
| 6,222,302 B1 | | 4/2001 | Imada et al. ................. 310/321 |
| 6,505,515 B1 | * | 1/2003 | Delaporte ..................... 73/714 |
| 6,668,649 B2 | * | 12/2003 | Ishitoko et al. ........... 73/504.12 |
| 6,739,201 B1 | * | 5/2004 | Tanner et al. ................. 73/826 |
| 2002/0020218 A1 | | 2/2002 | Ishitoko et al. ........... 73/504.12 |
| 2006/0185441 A1 | * | 8/2006 | Wang et al. ................... 73/801 |

FOREIGN PATENT DOCUMENTS

JP 10-065231 3/1998

(Continued)

OTHER PUBLICATIONS

"Shindo Kogaku" published by Yokendo and first-printed in 1976, in Section 4.6 "Plate vibration" in Chapter 4 "Free Vibration of distribution system", pp. 98-109 (w/English Translation).

(Continued)

*Primary Examiner*—Hezron E. Williams
*Assistant Examiner*—Jacques M. Saint-Surin
(74) *Attorney, Agent, or Firm*—Burr & Brown

(57) ABSTRACT

In an inspecting method of a piezoelectric/electrostrictive actuator having a piezoelectric/electrostrictive element and two or more electrodes, the frequency response characteristics is picked up when a vibration is given to the piezoelectric/electrostrictive actuator, and the amount of displacement of the piezoelectric/electrostrictive actuator is predicted by the frequency response characteristics. The piezoelectric/electrostrictive actuator is precisely inspected without dissolution and destruction and without actual driving as a product.

27 Claims, 27 Drawing Sheets

FOREIGN PATENT DOCUMENTS

| | | |
|---|---|---|
| JP | 11-168246 | 6/1999 |
| JP | 2002-5664 | 1/2002 |
| WO | 98/01737 | 1/1998 |
| WO | 01/31309 | 5/2001 |

OTHER PUBLICATIONS

"Kogyo Kiso Shindo-gaku" published by Yokendo and fourteenth-printed in 1989, in Chapter 9 "Lateral vibration of plainer plate", pp. 224-228 (w/English Translation).

* cited by examiner

DISTRIBUTION OF VIBRATIONS IN FIRST MODE
(m,n)=(1,1)

VIBRATING AREA
(±1.0 IS END OF VIBRATING PLATE, 0 IS IN CENTER)

INSPECTING METHOD OF ELASTIC BODY, INSPECTING APPARATUS THEREOF, AND DIMENSION PREDICTING PROGRAM THEREOF

BACKGROUND OF THE INVENTION

1. Field of the Invention

The present invention relates to an inspecting method, an inspecting apparatus, and a dimension predicting program of an elastic body with high precision, an inspecting method, an inspecting apparatus, and a dimension predicting program of a piezoelectric/electrostrictive actuator, and an inspecting method, an inspecting apparatus, and a dimension predicting program of a piezoelectric/electrostrictive sensor.

2. Description of the Related Art

Recently, the fields of optics, precision machines, and semiconductor manufacturing require a displacement control device for adjusting the length of optical path and the position of submicron order. In response to this requirement, a piezoelectric/electrostrictive device is developed, including a piezoelectric/electrostrictive actuator using the strain based on the inverse piezoelectric effect or electrostrictive effect upon applying an electric field to a ferroelectric member of an antiferroelectric member, and a piezoelectric/electrostrictive sensor using the charge generation upon applying the stress to the ferroelectric/antiferroelectric element based on the similar effects. The piezoelectric/electrostrictive device uses the charges or electric field induced by the strain of electric-field induction or stress as mentioned above. In particular, the piezoelectric/electrostrictive actuator has features that it is easily controlled for minute displacement, the mechanical/electrical energy conversion efficiency is higher, the power consumption is realized, and these thus contribute to the ultraprecise mounting and to the reduction in size and weight of product. Therefore, the application field might be enhanced.

The piezoelectric/electrostrictive actuator comprises a piezoelectric/electrostrictive operating unit structured by sequentially laminating a bottom electrode, a piezoelectric/electrostrictive element, and a top electrode on one surface of a ceramic base integrally formed by a thick supporting unit having a cavity and a vibrating unit for covering the cavity. In the above-mentioned piezoelectric/electrostrictive actuator, an electric field is generated between the top electrode and the bottom electrode, then, the piezoelectric/electrostrictive element containing a piezoelectric/electrostrictive material is deformed and the vibrating unit is further vertically displaced. The piezoelectric/electrostrictive actuator is applied as an actuator unit of a precision machine using the operation for displacing the vibrating unit. For example, the piezoelectric/electrostrictive actuator controls the on/off operation of a switch or controls the fluid as a micro pump by vertically deforming the vibrating unit.

When the piezoelectric/electrostrictive actuator is used as a switch or an actuator of a micro pump and the amount of displacement is not sufficiently large, the amount of stroke is not sufficient and the piezoelectric/electrostrictive actuator does not function as the switch, or the throughput of fluid is not sufficient in the micro pump. The fluid is not pulled out depending on the case. Further, upon using a set of a plurality of piezoelectric/electrostrictive actuators, the on/off operation of switch is unstable or the throughput of fluid is unstable when the amount of displacement of the plurality of piezoelectric/electrostrictive actuators varies. Thus, the quality of switch or micro pump deteriorates. Therefore, when the same voltage is applied (the same electric field is generated), the piezoelectric/electrostrictive actuator requires the vibrating unit with the amount of displacement that is a predetermined one or more and is uniform. Therefore, when the piezoelectric/electrostrictive actuator is shipped as a product, the amount of displacement of the vibrating unit must directly be inspected by a laser Doppler vibration-meter. However, the entire lots of the manufactured piezoelectric/electrostrictive actuators are inspected and then costs increase. Therefore, in place of this, another inspecting method is required.

Non-Patent Document 1: "Shindo Kogaku" published by Yokendo and first-printed in 1976, in Section 4.6 "Plate vibration" in Chapter 4 "Free vibration of distribution system" (pages 98 to 109)

Non-Patent Document 2: "Kogyo Kiso Shindo-gaku" published by Yokendo and fourteenth-printed in 1989, in Chapter 4 "Lateral vibration of plainer plate" (pages 224 to 228)

SUMMARY OF THE INVENTION

In response to the above-mentioned requests for the inspection of the piezoelectric/electrostrictive actuator, conventionally, the amount of displacement or uniformity of displacement is inspected by measuring the capacitance of a piezoelectric/electrostrictive element as a capacitor in the manufacturing process of the piezoelectric/electrostrictive actuator, upon applying the same voltage (the same electric field). According to the inspecting method, the piezoelectric/electrostrictive element of the piezoelectric/electrostrictive actuator is a displacement generating unit and, therefore, the electrode area, the distance between the electrodes, or the dielectric constant of the piezoelectric/electrostrictive element is totally equal based on a relation of a capacitance $C$ ($=\epsilon S/d$) when the capacitance is equal. Thus, the amount of displacement of the piezoelectric/electrostrictive element (or piezoelectric/electrostrictive operating unit) is equal and the amount of displacement of the vibrating unit is totally equal. Thus, the amount of displacement is not varied.

However, the above-mentioned conventional inspecting method does not necessarily have the high precision. Because it is considered that a component except for the piezoelectric/electrostrictive operating unit of the piezoelectric/electrostrictive actuator does not reflect advantages for inspection. Further, the piezoelectric/electrostrictive actuator is recently miniaturized and, thus, the minute deviation or variation in dimension seriously affects properties. The observation of cross section with destruction is required so as to inspect the minute deviation or variation in dimension and costs increase. Further, since the destruction is necessary for inspection, the shipped products cannot directly be inspected.

A device for directly inspecting the amount of displacement of the piezoelectric/electrostrictive actuator by a laser Doppler vibration-meter is expensive and the inspection time increases, thereby raising costs. Many skilled persons are required and the inspection time increases to detect the amount of positional displacement by the inspection of appearance using a microscope in a manufacturing process, and costs thus increase. In addition to increase the costs, the method for inspecting the amount of positional displacement with destruction does not enable the inspected device to directly be used as a product, and only the sampling inspection is possible. The above-mentioned problems are caused in a piezoelectric/electrostrictive sensor which requires the uniform sensor-sensitivity with the same design and specification.

The present invention is devised in consideration of the above-mentioned situations. It is an object of the present invention to provide a method for inspecting a piezoelectric/ electrostrictive device (piezoelectric/electrostrictive actuator or a piezoelectric/electrostrictive sensor) with high precision without the actual driving as a product and dissolution and destruction.

As a result of many researches, the amount of displacement of the vibrating unit in the above-mentioned piezoelectric/electrostrictive actuator greatly depends on elements of the mechanical property or form of the piezoelectric/electrostrictive actuator, such as rigidity of the overall piezoelectric/electrostrictive actuator including a base (including a vibrating unit and a supporting unit), the shape of vibrating unit, and forming position of the piezoelectric/electrostrictive operating unit to the vibrating unit.

Further, as a result of many researches, various frequency properties are checked upon vibrating the piezoelectric/electrostrictive actuator, and it is found that the elements of the mechanical property or form of the piezoelectric/electrostrictive actuator are predicted with high precision based on the frequency properties. Further, it is possible to structure a system for predicting the elements of the mechanical property or form of the piezoelectric/electrostrictive actuator, and it is found that the piezoelectric/electrostrictive actuator is predicted with high precision based on the predicted elements of the mechanical property or form of the piezoelectric/electrostrictive actuator. In addition, since the amount of displacement greatly depends on the elements of the mechanical property or form of the piezoelectric/electrostrictive actuator. Therefore, the amount of displacement of the vibrating unit in the piezoelectric/electrostrictive actuator is inspected with high precision.

Specifically, a predetermined relationship is established among a value of any frequency response characteristics depending on the design dimension of the piezoelectric/electrostrictive actuator, the dimensional deviation from a dimensional value for design of a specimen, and the amount of positional displacement. It is inspected, by obtaining the value of the frequency response characteristics, whether or not the dimensional deviation from the dimensional value for design of the specimen and the amount of positional displacement are within predetermined allowable values. Further, since a close relationship is established between the property of the amount of displacement of the piezoelectric/electrostrictive actuator and the dimensional deviation from the dimensional value for design, the amount of displacement is predicted from the frequency response characteristics and is converted for inspection.

In addition, as a result of many researches, one dimensional deviation of the piezoelectric/electrostrictive actuator, serving as a plate (plate-shaped member), depends on the peak height of resonant waveform corresponding to a vibrating mode of (1, 2) degree, and another dimensional deviation of the piezoelectric/electrostrictive actuator depends on a ratio of resonance frequency corresponding to vibrating modes of (3, 1) degree and (1, 1) degree. As mentioned above, it is found that a factor of dimensional deviation has a characteristic resonance of degree ((m, n) degree). Further, a vibrating mode of a specific degree (referred to as a 3.5-degree in the specification) which is not described in conventional documents exists and the resonance of the vibrating mode enables the prediction with excessively high precision of the dimensional deviation of the one part of the piezoelectric/electrostrictive actuator, serving as a plate member. In addition, the dimensional deviation is individually inspected or the amount of displacement of the piezoelectric/electrostrictive actuator is predicted and is inspected with high precision by obtaining a calculating formula based on the multiple linear regression analysis using the combination of the frequency properties.

Generally, as disclosed in Non-Patent Document 1 and Non-Patent Document 2, the vibration of the plate (plate-shaped member) is expressed as a vibrating mode of (m, n) degree. When the plate is quadrate or rectangular, a vibrating mode of (m, n) degree is expressed in accordance with the number of nodes of stationary waves in the longitudinal and lateral directions, and when the plate is disc-shaped, a vibrating mode of (m, n) degree is expressed in accordance with the number of nodes of stationary waves in the circumferential and diameter directions. In the specification, the vibrating mode without any nodes is expressed as a first mode, and the vibrating mode having one node is expressed as a second mode. That is, when the plate is rectangular, the vibrating mode having (m−1) nodes in the longitudinal direction and (n−1) nodes in the lateral direction is expressed as a vibrating mode of (m, n) degree. The vibrating mode of resonance frequency is specified by vibrating the plate by a resonance frequency, measuring the vibration at a plurality of points of the plate by a laser Doppler vibration-meter, totally analyzing the obtained vibration data, and observing the analyzing result on animation.

Similarly to the amount of displacement of the piezoelectric/electrostrictive actuator, the detecting sensitivity of the piezoelectric/electrostrictive sensor is inspected based on the foregoing. Further, the present invention is completed by finding that the dimensional inspecting method is applied to structures having an elastic body including a piezoelectric/electrostrictive device (piezoelectric/electrostrictive actuator or a piezoelectric/electrostrictive sensor). Specifically, the present invention provides the following means.

That is, it is one object of the present invention to provide inspecting method of an elastic body in a structure having two or more of elastic bodies which comprises picking up a frequency response characteristics of an elastic body when a vibration is given to a structure having two or more of elastic bodies, and predicting a dimension of said two or more of elastic bodies based on said frequency response characteristics.

The frequency response characteristics is obtained by directly measuring mechanical vibrations with a laser Doppler vibration-meter or an acceleration sensor upon vibrating the elastic body by a vibration exciter or piezoelectric/electrostrictive element. However, in the case of the piezoelectric/electrostrictive actuator and the piezoelectric/electrostrictive sensor, the measurement is inexpensive and fast by measuring electrical impedance or the frequency response characteristics of gain and phase with a network analyzer and an impedance analyzer. The foregoing is applied to the entire present invention (inspecting method of the piezoelectric/electrostrictive actuator, inspecting method of the piezoelectric/electrostrictive sensor, inspecting apparatus of the elastic body, inspecting apparatus of the piezoelectric/electrostrictive actuator, inspecting apparatus of the piezoelectric/electrostrictive sensor, dimension predicting program of the elastic body, prediction program of the amount of displacement of the piezoelectric/electrostrictive actuator, and inspecting method of the detecting sensitivity of the piezoelectric/electrostrictive sensor).

In the inspecting method of the elastic body according to the present invention, preferably, the frequency response characteristics is a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies of other degrees. Further, preferably, the dimension of the elastic body is predicted by using additionally a resonance frequency Fz of a degree other than the above-mentioned degrees in combination with one or more of the above-mentioned frequencies.

Preferably, the frequency response characteristics is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

Further, the dimension of the elastic body is predicted and estimated with high precision by multiple classification analysis based on the combination of the frequency properties.

The elastic body is easily inspected by determining whether or not a resonant peak of the resonance of a degree (m, n) appears, that is, determining whether or not the resonance of (m, n) degree is generated (this is applied to any embodiments of the present invention).

In the specification, the resonant waveform of the resonance of (m, n) degree is a waveform (curve) indicating the periphery of the resonant peak corresponding to the vibrating mode of (m, n) degree among waveforms indicated as the frequency properties of a predetermined frequency band. Although the frequency response characteristic is not limited, it includes a transmission property of mechanical vibrations, an electrical-impedance property, an electric transfer property, and an electric reflecting property. The frequency response characteristic is expressed with a chart using a frequency, as the abscissa, and gain and phase, impedance and phase, or admittance and phase, as the ordinate. The mechanical resonance is different as phenomena from electrical resonance. In the piezoelectric/electrostrictive actuator or piezoelectric/electrostrictive sensor, the mechanical resonance and the electrical resonance are observed with the matching resonance frequency. This phenomenon is applied to a piezoelectric resonator or a piezoelectric filter.

In the chart indicating the frequency response characteristics, the resonance of (m, n) degree is specified at a crest and/or trough portion having the peak of the resonant waveform. The resonant waveform corresponds to a waveform indicating the periphery of the crest and/or trough portion. The area of resonant waveform corresponds to an area of the crest and/or trough portion to a line as the base without the peak in the chart indicating the frequency response characteristics. The peak height of the resonant waveform is a value of the peak height of the crest and/or trough portion. The ordinate may be any of frequency properties, such as gain, impedance, admittance, and phase. However, preferably, the ordinate is phase in the case of electrical vibrations and further is gain in the case of mechanical vibrations. Because the line as the base is relatively flat and data processing is thus easy. The difference between the maximum value and the minimum value of the resonant waveform is preferably used in the chart using the impedance or admittance as the ordinate. In the case of using the impedance or admittance as the ordinate, the basic line becomes an upward-sloping or downward-sloping curve and/or a straight line, the resonance and the non-resonance are combined, the peak exists at the crest and the trough portion, and the difference between the crest portion and the trough portion is used as a property value for predicting the dimensional deviation or the amount of displacement.

In the inspecting method of the elastic body according to the present invention, preferably, the dimension of the elastic body is the amount of deviation between two arbitrary elastic bodies among two or more elastic bodies forming the structure. Preferably, the dimension of the elastic body is the amount of undulation of one arbitrary elastic body among two or more elastic bodies forming the structure.

Next, according to the present invention, there is provided an inspecting method of a piezoelectric/electrostrictive actuator having a piezoelectric/electrostrictive element and two or more electrodes, comprising the step of picking up a frequency response characteristics upon vibrating the piezoelectric/electrostrictive actuator and predicting the amount of displacement of the piezoelectric/electrostrictive actuator by the frequency response characteristics.

In the inspecting method of the piezoelectric/electrostrictive actuator according to the present invention, preferably, the frequency response characteristics is a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies of other degrees.

In the inspecting method of the piezoelectric/electrostrictive actuator according to the present invention, preferably, a resonance frequency Fz of one or more and/or a capacitance CP of the piezoelectric/electrostrictive element is added to a frequency ratio FR of one or more and/or a frequency difference FD of one or more, and the amount of displacement of the piezoelectric/electrostrictive actuator is predicted by using any of the frequency properties or combining two or more of the frequency properties.

Preferably, the frequency response characteristics is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

Further, the dimension of elastic body is predicted and estimated with high precision by multiple classification analysis based on the combination of the frequency properties.

Next, according to the present invention, there is provided an inspecting method of a piezoelectric/electrostrictive sensor having a piezoelectric/electrostrictive element and two or more electrodes, comprising the step of picking up a frequency response characteristics when a vibration is given to the piezoelectric/electrostrictive actuator and predicting a detecting sensitivity of the piezoelectric/electrostrictive sensor based on the frequency response characteristics.

In the inspecting method of the piezoelectric/electrostrictive sensor according to the present invention, preferably, the frequency response characteristics is a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies of other degrees.

In the inspecting method of the piezoelectric/electrostrictive sensor according to the present invention, preferably, a resonance frequency Fz of one or more and/or a capacitance CP of the piezoelectric/electrostrictive element is added to the frequency ratio FRxy of one or more and/or the frequency difference FDxy of one or more, and the detecting sensitivity of the piezoelectric/electrostrictive sensor is predicted.

Preferably, the frequency response characteristics is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

Further, the detecting sensitivity of the piezoelectric/electrostrictive sensor is predicted and estimated with high precision by multiple classification analysis based on the combination of the frequency properties.

Next, according to the present invention, there is provided an inspecting apparatus of an elastic body in a structure having two or more of elastic bodies, comprising means for picking up a frequency response characteristics upon vibrating the structure and predicting the dimension of the elastic body by the frequency response characteristics.

In the inspecting apparatus of the elastic body according to the present invention, preferably, the frequency response characteristics is a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies of other degrees. Further, preferably, the inspecting apparatus of the elastic body comprises means for predicting the dimension of the elastic body by adding a resonance frequency Fz, as the frequency response characteristics and by using any of the frequency properties or combining two or more of the frequency properties.

Preferably, the frequency response characteristics is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

In the inspecting apparatus of the elastic body according to the present invention, preferably, the dimension of the elastic body is the amount of deviation of two arbitrary elastic bodies among two or more elastic bodies forming the structure. Further, preferably, the dimension of the elastic body is the amount of undulation of one arbitrary elastic body among two or more elastic bodies forming the structure.

Next, according to the present invention, there is provided an inspecting apparatus of a piezoelectric/electrostrictive actuator having a piezoelectric/electrostrictive element and two or more electrodes, comprising means for picking up a frequency response characteristics when a vibration is given to the piezoelectric/electrostrictive actuator and predicting the amount of displacement of the piezoelectric/electrostrictive actuator based on the frequency response characteristics.

In the inspecting apparatus of the piezoelectric/electrostrictive actuator according to the present invention, preferably, the frequency response characteristics is a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies of other degrees.

Preferably, the inspecting apparatus of the piezoelectric/electrostrictive actuator according to the present invention comprises means for predicting the amount of displacement of the piezoelectric/electrostrictive actuator by using additionally at least one of a resonance frequency Fz of a degree other than the above-mentioned degrees and/or at least one of capacitances CP of the piezoelectric/electrostrictive element to the combination of at least one of the frequency ratios FRxys and/or at least one of frequency differences FDxys.

Preferably, the frequency response characteristics is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

Next, according to the present invention, there is provided an inspecting apparatus of a piezoelectric/electrostrictive sensor having a piezoelectric/electrostrictive element and two or more electrodes, comprising means for picking up a frequency response characteristic upon vibrating the piezoelectric/electrostrictive sensor and predicting a detecting sensitivity of the piezoelectric/electrostrictive sensor by the frequency response characteristics.

In the inspecting apparatus of the piezoelectric/electrostrictive sensor according to the present invention, preferably, the frequency response characteristics is one of a resonance frequency Fx of a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies of other degrees.

Preferably, the second inspecting apparatus of the piezoelectric/electrostrictive sensor according to the present invention comprises means for predicting the detecting sensitivity of the piezoelectric/electrostrictive sensor by using additionally at least one of a resonance frequency Fz of a degree other than the above-mentioned degrees and/or at least one of capacitances CP of the piezoelectric/electrostrictive sensor to the combination of at least one of the frequency ratios FRxys and/or at least one of frequency differences FDxys.

Preferably, the frequency response characteristics is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

Next, according to the present invention, there is provided a dimension predicting program of an elastic body in a structure having two or more of elastic bodies, for enabling a computer to function as: means for inputting a measurement value of a frequency response characteristics of the structure whose predicted dimension is calculated; means for obtaining a predicted dimension of the elastic body to the structure based on a calculating formula of the predicted dimension; and means for outputting the obtained predicted dimension of the elastic body to the structure.

In the dimension predicting program of the elastic body according to the present invention, preferably, the predicted dimension of the elastic body is the amount of deviation of two arbitrary elastic bodies among two or more elastic bodies forming the structure. Preferably, the predicted dimension of the elastic body is the amount of undulation of one arbitrary elastic body among two or more elastic bodies forming the structure.

In order to predict the dimension of an elastic body of a structure having two or more of the elastic bodies, preferably, a dimension predicting program of an elastic body according to the present invention enables a computer to function as: means for inputting a first resonance frequency F1 (the frequency response characteristics) upon vibrating the structure; means for inputting a resonance frequency Fn (the frequency response characteristics) of an n-th degree, serving as one or more of high degree frequency, upon vibrating the structure; means for obtaining a frequency ratio FRn (FRn=Fn/F1) of one or more by the first resonance frequency F1 and the resonance frequency Fn (the frequency response characteristics) of an n-th degree, serving as a high degree, of one or more; means for obtaining a predicted dimension of the elastic body of the structure based on the following [Formula 1] (calculating formula of the predicted dimension); and means for outputting the obtained predicted dimension of the elastic body of the structure.

$$\text{Predicted dimension } M1 = \sum_{x=0}^{x=x'} \sum_{n} a_{xn}(FRn)^x (x' = 1, 2, \dots) \quad \text{[Formula 1]}$$

Preferably, a dimension predicting program of an elastic body according to the present invention, specifically, to predict the dimension of the elastic body of a structure having two or more elastic bodies, enables a computer to function as: means for inputting a resonance frequency Fm (the frequency response characteristics) of a first or more degrees upon vibrating the structure; means for obtaining a predicted dimension of the elastic body of the structure based on [Formula 2] (calculating formula of the predicted dimension); and means for outputting the obtained predicted dimension of the elastic body of the structure.

$$\text{Predicted dimension } M2 = \sum_{w=0}^{w=w'} \sum_{m} d_{wm}(Fm)^w (w' = 1, 2, \dots) \quad \text{[Formula 2]}$$

Next, according to the present invention, in order to predict the amount of displacement of a piezoelectric/electrostrictive actuator having a piezoelectric/electrostrictive element and two or more electrodes, there is provided a prediction program of the amount of displacement of a piezoelectric/electrostrictive actuator that enables a computer to function as: means for inputting a frequency response characteristics of the piezoelectric/electrostrictive actuator whose predicted amount of displacement is calculated; means for obtaining the predicted amount of displacement of the piezoelectric/electrostrictive actuator based on a calculating formula of the predicted amount of displacement; and means for outputting the obtained predicted amount of displacement of the piezoelectric/electrostrictive actuator.

In the prediction program of the amount of displacement of the piezoelectric/electrostrictive actuator according to the present invention, it is possible to input, as the frequency response characteristics, an area, a peak height, and a difference between a maximum value and a minimum value of a resonant waveform of a first resonance and/or a resonance of an n-th degree, serving as a high degree, of one or more, and an area ratio, a ratio of peak height, and a ratio of difference between the maximum value and the minimum value between the obtained resonant waveform of the first resonance and the obtained resonant waveform of resonance of an n-th degree, serving as a high degree of one or more.

Preferably, in order to predict the amount of displacement of the piezoelectric/electrostrictive actuator having the piezoelectric/electrostrictive element and two or more electrodes according to the present invention, the prediction program of the amount of displacement of the piezoelectric/electrostrictive actuator according to the present invention enables a computer to function as: means for inputting a first resonance frequency F1 (the frequency response characteristics) upon vibrating the piezoelectric/electrostrictive actuator; means for inputting a resonance frequency Fn (the frequency response characteristics) of an n-th degree, serving as a high degree, of one or more, upon vibrating the piezoelectric/electrostrictive actuator; means for obtaining a frequency ratio FRn (FRn=Fn/F1) of one or more by the first resonance frequency F1 and the resonance frequency Fn (the frequency response characteristics) of an n-th degree, of one or more; means for obtaining the predicted amount of displacement of the piezoelectric/electrostrictive actuator based on the following [Formula 3] (calculating formula of the predicted amount of displacement); and means for outputting the obtained predicted amount of displacement of the piezoelectric/electrostrictive actuator.

$$\text{Predicted amount } M3 \text{ of displacement} = \sum_{x=0}^{x=x'} \sum_{n} a_{xn}(FRn)^x (x' = 1, 2, \dots) \quad \text{[Formula 3]}$$

Preferably, specifically, in order to predict the amount of displacement of the piezoelectric/electrostrictive actuator having a piezoelectric/electrostrictive element and two or more electrodes, the prediction program of the amount of displacement of the piezoelectric/electrostrictive actuator according to the present invention enables a computer to function as: means for inputting a first resonance frequency F1 (the frequency response characteristics) upon vibrating the piezoelectric/electrostrictive actuator; means for inputting a resonance frequency Fn (the frequency response characteristics) of an n-th degree, serving as a high degree, of one or more, upon vibrating the piezoelectric/electrostrictive actuator; means for inputting a capacitance CP of the piezoelectric/electrostrictive element; means for obtaining a frequency ratio FRn (FRn=Fn/F1) equal to one or more by the first resonance frequency F1 and the resonance frequency Fn (the frequency response characteristics) of n-th degree, serving as a high degree of one or more; means for obtaining the predicted amount of displacement of the piezoelectric/electrostrictive actuator based on the following [Formula 4] (calculating formula of the predicted amount of displacement); and means for outputting the obtained the predicted amount of displacement of the piezoelectric/electrostrictive actuator.

$$\text{Predicted amount } M4 \text{ of displacement} = \sum_{x=0}^{x=x'} \sum_{n} a_{xn}(FRn)^x + \sum_{z=0}^{z=z'} c_z(CP)^z (x' = 1, 2, \ldots, z' = 1, 2, \ldots) \quad [\text{Formula 4}]$$

In order to predict the amount of displacement of the piezoelectric/electrostrictive actuator, preferably, the prediction program of the amount of displacement of piezoelectric/electrostrictive actuator according to the present invention enables a computer to function as: means for inputting a resonance frequency Fm (the frequency response characteristics) of an m degree of one or more upon vibrating the piezoelectric/electrostrictive actuator; means for obtaining the predicted amount of displacement of the piezoelectric/electrostrictive actuator based on [Formula 5] (calculating formula of the predicted amount of displacement); and means for outputting the obtained the predicted amount of displacement of the piezoelectric/electrostrictive actuator.

$$\text{Predicted amount } M5 \text{ of displacement} = \sum_{w=0}^{w=w'} \sum_{m} d_{wm}(Fm)^w (w' = 1, 2, \ldots) \quad [\text{Formula 5}]$$

In order to predict the amount of displacement of the piezoelectric/electrostrictive actuator having the piezoelectric/electrostrictive element and two or more electrodes, preferably, the prediction program of the amount of displacement of the piezoelectric/electrostrictive actuator according to the present invention enables a computer to function as: means for inputting a first resonance frequency F1 (the frequency response characteristics) upon vibrating the piezoelectric/electrostrictive actuator; means for inputting a resonance frequency Fn (the frequency response characteristics) of an n-th degree, serving as a high degree, of one or more, upon vibrating the piezoelectric/electrostrictive actuator; means for obtaining a frequency ratio FRn (FRn=Fn/F1) of one or more by the first resonance frequency F1 and the resonance frequency Fn (the frequency response characteristics) of an n-th degree, serving as a high degree, of one or more; means for obtaining the predicted amount of displacement of the piezoelectric/electrostrictive actuator based on the following [Formula 6] (calculating formula of the predicted amount of displacement); and means for outputting the obtained the predicted amount of displacement of the piezoelectric/electrostrictive actuator.

$$\text{Predicted amount } M6 \text{ of displacement} = \sum_{x=0}^{x=x'} \sum_{n} a_{xn}(FRn)^x + \sum_{w=0}^{w=w'} \sum_{m} d_{wm}(Fm)^w (x' = 1, 2, \ldots, w' = 1, 2, \ldots) \quad [\text{Formula 6}]$$

In order to predict the amount of displacement of the piezoelectric/electrostrictive actuator having the piezoelectric/electrostrictive element and two or more electrodes, preferably, the prediction program of the amount of displacement of the piezoelectric/electrostrictive actuator according to the present invention enables a computer to function as: means for inputting a first resonance frequency F1 (the frequency response characteristics) upon vibrating the piezoelectric/electrostrictive actuator; means for inputting a resonance frequency Fn (the frequency response characteristics) of an n-th degree, serving as a high degree, of one or more, upon vibrating the piezoelectric/electrostrictive actuator; means for inputting a capacitance CP of the piezoelectric/electrostrictive element; means for obtaining a frequency ratio FRn (FRn=Fn/F1) of one or more by the first resonance frequency F1 and the resonance frequency Fn (the frequency response characteristics) of an n-th degree, serving as a high degree, of one or more; means for obtaining the predicted amount of displacement of the piezoelectric/electrostrictive actuator based on the following [Formula 7] (calculating formula of the predicted amount of displacement); and means for outputting the obtained the predicted amount of displacement of the piezoelectric/electrostrictive actuator.

$$\text{Predicted amount } M7 \text{ of displacement} = \sum_{x=0}^{x=x'} \sum_{n} a_{xn}(FRn)^x + \sum_{w=0}^{w=w'} \sum_{m} d_{wm}(Fm)^w + \sum_{z=0}^{z=z'} c_z(CP)^z (x' = 1, 2, \ldots, w' = 1, 2, \ldots, z' = 1, 2, \ldots) \quad [\text{Formula 7}]$$

Next, according to the present invention, in order to predict a detecting sensitivity of a piezoelectric/electrostrictive sensor having a piezoelectric/electrostrictive element and two or more electrodes, there is provided a prediction program of a detecting sensitivity of a piezoelectric/electrostrictive sensor that enables a computer to function as: means for inputting a frequency response characteristics of the piezoelectric/electrostrictive sensor whose predicted detecting sensitivity is calculated; means for obtaining the predicted detecting sensitivity of the piezoelectric/electrostrictive sensor based on a calculating formula of the detecting sensitivity; and means for outputting the obtained predicted detecting sensitivity of the piezoelectric/electrostrictive sensor.

In the prediction program of the detecting sensitivity of the piezoelectric/electrostrictive sensor according to the present invention, it is possible to input, as the frequency response characteristics, an area, a peak height, a difference between a maximum value and a minimum value of a resonant waveform of a first resonance and/or a resonance of an n-th degree, serving as a high degree, of one or more, and an area ratio, a ratio of peak height, and a ratio of difference between the maximum value and the minimum value between the obtained resonant waveform of the first resonance and the obtained resonant waveform of resonance of an n-th degree, serving as a high degree of one or more.

In order to predict the detecting sensitivity of the piezoelectric/electrostrictive sensor having the piezoelectric/electrostrictive element and two or more electrodes, preferably, the prediction program of the detecting sensitivity of the piezoelectric/electrostrictive sensor according to the present invention enables a computer to function as: means for inputting a first resonance frequency F1 (the frequency response characteristics) upon vibrating the piezoelectric/electrostrictive sensor; means for inputting a resonance frequency Fn (the frequency response characteristics) of an n-th degree, serving as a high degree, of one or more, upon vibrating the piezoelectric/electrostrictive sensor; means for obtaining a frequency ratio FRn (FRn=Fn/F1) of one or more by the first resonance frequency F1 and the resonance frequency Fn (the frequency response characteristics) of an n-th degree, serving as a high degree, of one or more; means for obtaining a detecting sensitivity for prediction of the piezoelectric/electrostrictive sensor based on the following [Formula 8] (calculating formula of the detecting sensitivity for prediction); and means for outputting the obtained detecting sensitivity for prediction of the piezoelectric/electrostrictive sensor.

$$\text{Predicted detecting sensitivity } M8 = \sum_{x=0}^{x=x'} \sum_{n} a_{xn}(FRn)^x (x' = 1, 2, \dots) \quad \text{[Formula 8]}$$

In order to predict the detecting sensitivity of the piezoelectric/electrostrictive sensor having the piezoelectric/electrostrictive element and two or more electrodes, preferably, the prediction program of the detecting sensitivity of the piezoelectric/electrostrictive sensor according to the present invention enables a computer to function as: means for inputting a first resonance frequency F1 (the frequency response characteristics) upon vibrating the piezoelectric/electrostrictive sensor; means for inputting a resonance frequency Fn (the frequency response characteristics) of an n-th degree, serving as a high degree, of one or more, upon vibrating the piezoelectric/electrostrictive sensor; means for inputting a capacitance CP of the piezoelectric/electrostrictive element; means for obtaining a frequency ratio FRn (FRn=Fn/F1) of one or more by the first resonance frequency F1 and the resonance frequency Fn (the frequency response characteristics) of an n-th degree, serving as a high degree, of one or more; means for obtaining the predicted detecting sensitivity of the piezoelectric/electrostrictive sensor based on the following [Formula 9] (calculating formula of the predicted detecting sensitivity); and means for outputting the obtained the predicted detecting sensitivity of the piezoelectric/electrostrictive sensor.

$$\text{Predicted detecting sensitivity } M9 = \sum_{x=0}^{x=x'} \sum_{n} a_{xn}(FRn)^x + \sum_{z=0}^{z=z'} c_z(CP)^z (x' = 1, 2, \dots, z' = 1, 2, \dots) \quad \text{[Formula 9]}$$

The formulae of program according to the present invention are used in methods according to the present invention. For example, the dimension of elastic body is predicted by the frequency ratio FRn of one or more according to the inspecting method of the elastic body according to the present invention, and the prediction uses [Formula 1] of the dimension predicting program of the elastic body according to the present invention.

In the inspecting method and inspecting apparatus of the elastic body according to the present invention, a part of the structure comprising two or more elastic bodies is not the basis for inspection, but the entire structure is minutely vibrated, then, the dimension of the elastic body, such as the amount of deviation between the two elastic bodies of the structure or the amount of undulation of one elastic body is predicted based on an area of a resonant waveform of a resonance of one degree and/or a resonance of another degree, a peak height, a difference between a maximum value and a minimum value, and an area ratio, height ratio of the peak, and a ratio of difference between the maximum value and the minimum value between the obtained resonant waveform of the resonance of the one degree and the obtained resonant waveform of the resonance of the other degree. Therefore, the inspection has high precision irrespective of experience. The accurate determination is fast because of inspection without destruction.

In the inspecting method and inspecting apparatus of the piezoelectric/electrostrictive actuator according to the present invention, with respect to the piezoelectric/electrostrictive actuator comprising the piezoelectric/electrostrictive element and the two or more electrodes, only the capacitance of the piezoelectric/electrostrictive element, serving as a part of the piezoelectric/electrostrictive actuator, but the entire piezoelectric/electrostrictive actuator is actually vibrated, then, the amount of displacement of piezoelectric/electrostrictive actuator is predicted based on the resonance frequency of one degree, the resonance frequency of another degree, the frequency ratio and the frequency difference obtained by the resonance frequency of the one degree and the resonance frequency of the other degree, the peak height, the area, the difference between a maximum value and a minimum value of the resonant waveform of one degree, and the ratio of peak height, the difference in peak height, the area ratio, and the area difference between the resonant waveform of the one degree and the resonant waveform of the other degree. Therefore, the inspection has high precision irrespective of experience. The accurate determination is fast because of inspection without destruction. Further, an error of shipping of undesired products is prevented.

In the inspecting method and the inspecting apparatus of the piezoelectric/electrostrictive sensor according to the present invention, with respect to the piezoelectric/electrostrictive sensor comprising the piezoelectric/electrostrictive element and the two or more electrodes, only the capacitance of the piezoelectric/electrostrictive element, serving as a part of the piezoelectric/electrostrictive sensor, but the entire piezoelectric/electrostrictive sensor is actually vibrated, then, the detecting sensitivity of piezoelectric/electrostrictive sensor is predicted based on the resonance frequency of one degree, the resonance frequency of another degree, the frequency ratio and the frequency difference obtained by the resonance frequency of the one degree and the resonance frequency of the other degree, the peak height, the area, the difference between a maximum value and a minimum value of the resonant waveform of the one degree, and the ratio of peak height, the difference in peak height, the area ratio, and the area difference between the resonant waveform of the one degree and the resonant waveform of the other degree. Therefore, the inspection has high precision irrespective of experience. The accurate determination is fast because of the inspection without destruction. Further, an error of shipping of undesired products is prevented.

BRIEF DESCRIPTION OF THE DRAWINGS

FIG. 6($b$) is a cross-sectional view showing an example of the piezoelectric/electrostrictive actuator as the actuator unit of the micro switch, further showing a conductive (ON) state;

FIG. 15($b$) is a perspective view showing another example of the piezoelectric/electrostrictive actuator;

FIG. 16($b$) is a top view showing another example of the shape of the vibrating unit in the piezoelectric/electrostrictive actuator;

FIG. 16($c$) is a top view showing another example of the shape of the vibrating unit in the piezoelectric/electrostrictive actuator;

FIG. 16($d$) is a top view showing another example of the shape of the vibrating unit in the piezoelectric/electrostrictive actuator;

FIG. 16($e$) is a top view showing another example of the shape of the vibrating unit in the piezoelectric/electrostrictive actuator;

FIG. 17($b$) is a diagram showing the structure of another example of the frequency response characteristics measurement system;

FIG. 19($b$) is a diagram showing the structure of another example of the frequency response characteristics measurement system;

FIG. 22($b$) is a diagram showing the distribution of vibrations in a vibrating mode A of a high-degree peak;

FIG. 22($c$) is a diagram showing the distribution of vibrations in a vibrating mode B of a high-degree peak;

FIG. 24($b$) is a chart showing another example of the frequency response characteristics of the piezoelectric/electrostrictive actuator;

FIG. 24($c$) is a chart showing another example of the frequency response characteristics of the piezoelectric/electrostrictive actuator;

FIG. 25($b$) is a chart showing another example of the frequency response characteristics of the piezoelectric/electrostrictive actuator;

FIG. 25($c$) is a chart showing another example of the frequency response characteristics of the piezoelectric/electrostrictive actuator;

Figure 1:
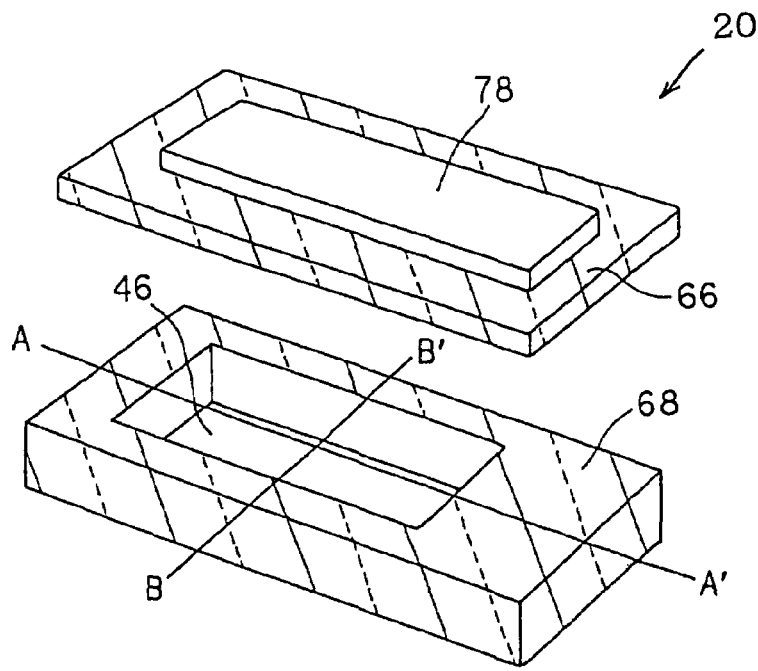
FIG. 1 is a perspective view showing an example of a piezoelectric/electrostrictive actuator, separating a vibrating unit and a supporting unit.

The followings are given to explain the meanings of the respective numerical references.
1: central processing unit,
2: storage device,
4: input device,
5: output device,
10: computer system,
20, 30, 40, 50, 51: piezoelectric/electrostrictive actuator,
44: substrate,
46: cavity,
66: vibrating unit,
68: supporting unit,
73: intermediate electrode,
74: upper electrode,
77: lower electrode,
78: piezoelectric/electrostrictive operating unit, and
79: piezoelectric/electrostrictive element.

DESCRIPTION OF THE PREFERRED EMBODIMENTS

Hereinbelow, an embodiment of the present invention will be described with reference to the drawings. The present invention is not limited to the embodiment and can variously be modified based on the acknowledgement of one skilled person without departing the essentials of the present invention. For example, the drawings express the preferable embodiment of the present invention, and the present invention is not limited by information in the drawings and the embodiment with reference to the drawings. In the employment and verification of the present invention, the means similar to that described in the specification or identical means is used and preferable means is described hereinbelow. In the specification, the present invention entirely relates to an inspecting method, an inspecting apparatus, and a dimension predicting program of an elastic body with high precision, an inspecting method, an inspecting apparatus, and a dimension predicting program of a piezoelectric/electrostrictive actuator, and an inspecting method, an inspecting apparatus, and a dimension predicting program of a piezoelectric/electrostrictive sensor.

Figure 2:
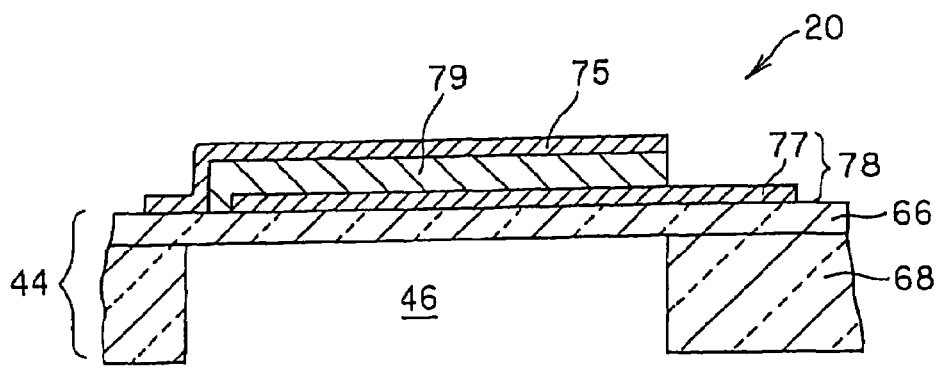
FIG. 2 is a cross-sectional view showing an AA' cross-section including the vibrating unit and a piezoelectric/electrostrictive operating unit in the piezoelectric/electrostrictive actuator shown in FIG. 1.
Figure 3:
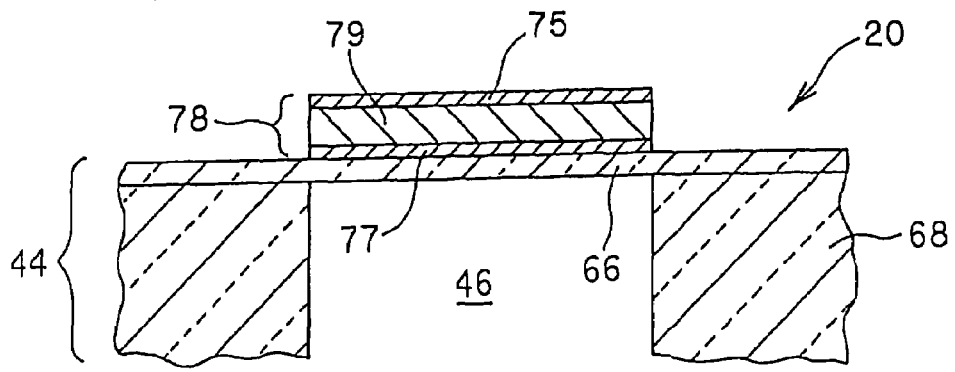
FIG. 3 is a cross-sectional view showing a BB' cross-section including the vibrating unit and the piezoelectric/electrostrictive operating unit in the piezoelectric/electrostrictive actuator shown in FIG. 1.

First, a description is given of a piezoelectric/electrostrictive actuator, serving as targets of an inspecting method and an inspecting apparatus and of a prediction program of the amount of displacement of the piezoelectric/electrostrictive actuator. FIGS. 1 to 5 are diagrams showing one example of the piezoelectric/electrostrictive actuator. FIG. 1 is a perspective view showing an example of a piezoelectric/electrostrictive actuator, separating a vibrating unit 66 and a supporting unit 68. FIG. 2 is a cross-sectional view showing an AA' cross-section including the vibrating unit 66 and a piezoelectric/electrostrictive operating unit 78 of the piezoelectric/electrostrictive actuator shown in FIG. 1. FIG. 3 is a cross-sectional view showing a BB' cross-section shown in FIG. 1. A piezoelectric/electrostrictive actuator 20 shown in FIGS. 1 to 3 comprises a base 44 and the piezoelectric/electrostrictive operating unit 78. The base 44 is structured by integrally forming the thick supporting unit 68 having a cavity 46 and the vibrating unit 66 which covers the cavity 46. The piezoelectric/electrostrictive operating unit 78 comprises: a piezoelectric/electrostrictive element 79; a top electrode 75 formed onto one surface of the piezoelectric/electrostrictive element 79; and a bottom electrode 77 formed onto another surface of the piezoelectric/electrostrictive element 79. Further, the piezoelectric/electrostrictive operating unit 78 is arranged onto one surface of the base 44 so that the bottom electrode 77 comes into contact with the vibrating unit 66. The piezoelectric/electrostrictive actuator has the above-mentioned structure, and the base and the piezoelectric/electrostrictive element usually contain a ceramic material (piezoelectric/electrostrictive material), and the electrode contains a metallic material (conductive material). The ceramic material and the metallic material are elastic materials and, therefore, the piezoelectric/electrostrictive element and the base are elastic members. The piezoelectric/electrostrictive actuator has a structure having two or more elastic bodies.

Figure 6A:
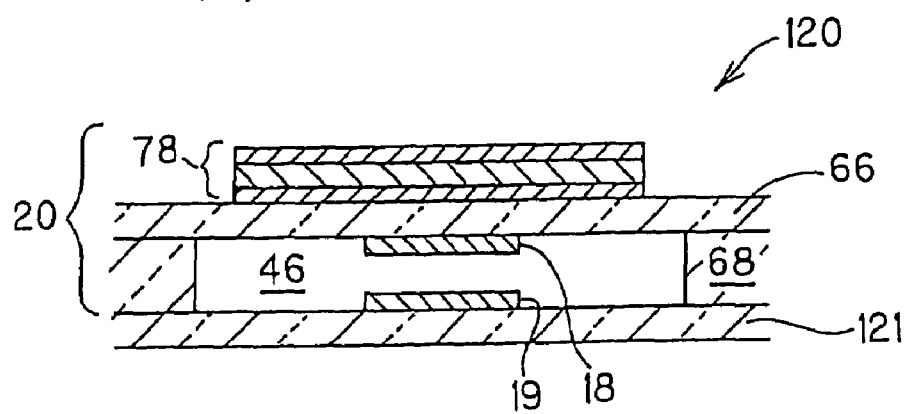
FIG. 6($a$) is a cross-sectional view showing an example of the piezoelectric/electrostrictive actuator as an actuator unit of a micro switch, further showing a non-conductive (OFF) state.
Figure 6B:
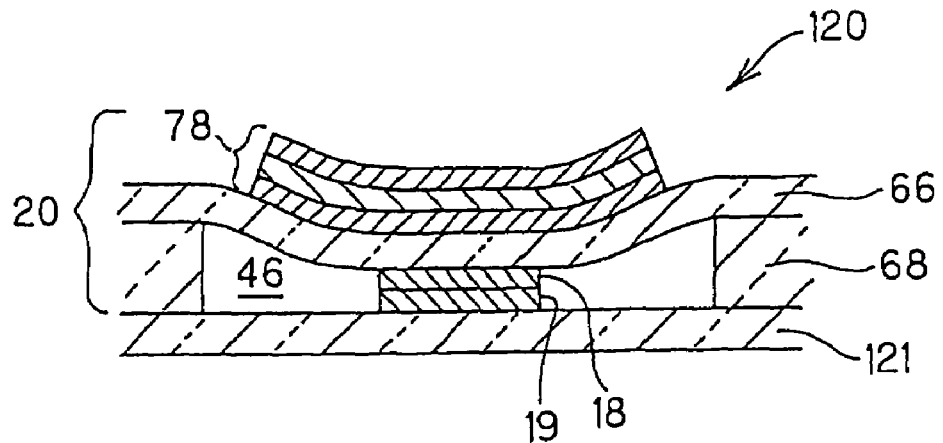

In a piezoelectric/electrostrictive actuator 20, an electric field is generated between the top electrode 75 and the bottom electrode 77 and then the piezoelectric/electrostrictive element 79 containing a piezoelectric/electrostrictive material is displaced, thereby deforming the vibrating unit 66. The operation enables the piezoelectric/electrostrictive actuator 20 to be used as an actuator unit of a precision machine. FIGS. 6(a) and 6(b) are cross-sectional views showing examples of the piezoelectric/electrostrictive actuator, serving as an actuator unit of a micro switch. A micro switch 120 shown in FIGS. 6(a) and 6(b) has a switch electrode 18 in the cavity 46 of the piezoelectric/electrostrictive actuator 20, and further has a terminal plate 121 to cover the cavity 46. A terminal plate 121 has a switch electrode 19 facing a switch electrode 18. When the vibrating unit 66 is not deformed, the switch electrodes 18 and 19 are non-conductive (OFF) (refer to FIG. 6(a)). However, when the piezoelectric/electrostrictive element 79 is displaced and the vibrating unit 66 is deformed, the switch electrodes 18 and 19 are conductive (ON) (refer to FIG. 6(b)).

Figure 7:
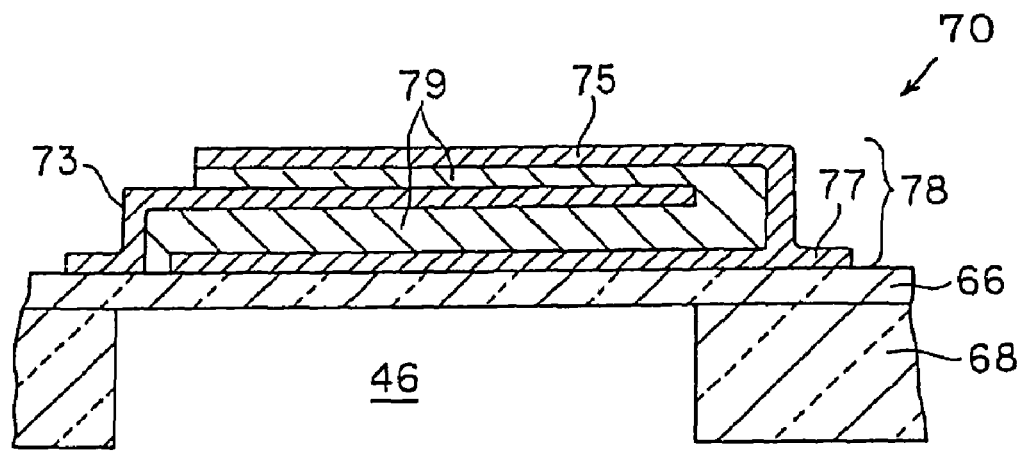
FIG. 7 is a cross-sectional view showing one example of the piezoelectric/electrostrictive actuator.
Figure 8:
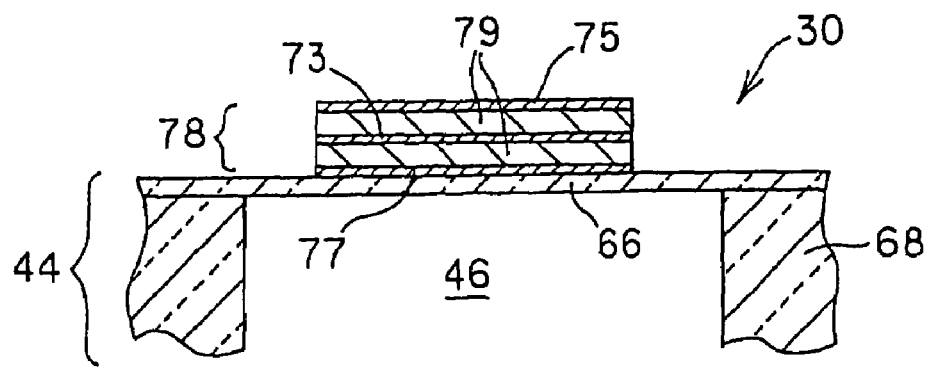
FIG. 8 is a cross-sectional view showing another example of the piezoelectric/electrostrictive actuator.
Figure 12:
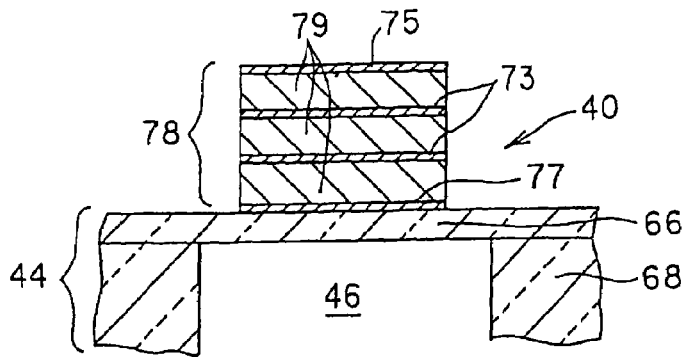
FIG. 12 is a cross-sectional view showing another example of the piezoelectric/electrostrictive actuator.

In addition to the piezoelectric/electrostrictive actuator 20 having one layer of the piezoelectric/electrostrictive element, as the piezoelectric/electrostrictive actuator, piezoelectric/electrostrictive actuators 70, 30, and 40 are shown in cross-sectional views in FIGS. 7, 8, and 12. FIG. 7 is a cross-sectional view showing the cross section shown in FIG. 2. FIGS. 8 and 12 are cross-sectional views showing the cross section shown in FIG. 3. The piezoelectric/electrostrictive actuators 70, 30, and 40 shown in FIGS. 7, 8, and 12 comprise the base 44 and the piezoelectric/electrostrictive operating unit 78. The base 44 is structured by integrally forming the thick supporting unit 68 having the cavity 46 and the vibrating unit 66 for covering the cavity 46, and this structure in the piezoelectric/electrostrictive actuators 30, 40, and 70 is common to the piezoelectric/electrostrictive actuator 20. However, the piezoelectric/electrostrictive actuator 70 and the piezoelectric/electrostrictive actuator 30 (refer to FIGS. 7 and 8) comprise two layers of the piezoelectric/electrostrictive elements 79 sandwiched among the top electrode 75, an intermediate electrode 73, and the bottom electrode 77 and the piezoelectric/electrostrictive actuator 40 (refer to FIG. 12) comprises three layers of the piezoelectric/electrostrictive elements 79, and these are different from the piezoelectric/electrostrictive actuator 20. In the specification, for the purpose of convenience, an electrode on the most nearest position of the vibrating unit 66 of the piezoelectric/electrostrictive operating unit 78 is referred to as a bottom electrode, and an electrode on the farthest position of the vibrating unit 66 is referred to as a top electrode. When a plurality of piezoelectric/electrostrictive elements is laminated, an electrode other than the top electrode and the bottom electrode is referred to as an intermediate electrode.

Figure 15A:
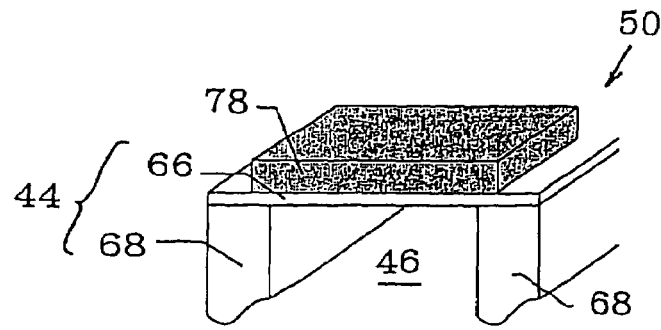
FIG. 15($a$) is a perspective view showing another example of the piezoelectric/electrostrictive actuator.
Figure 15B:
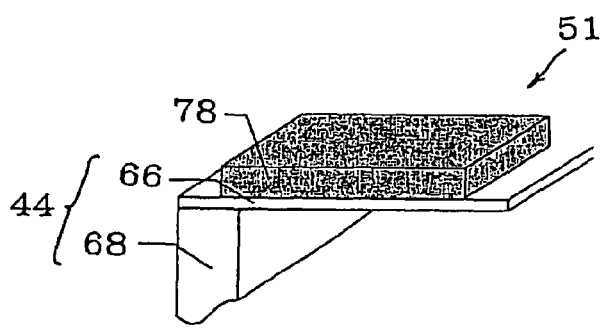
Figure 16A:
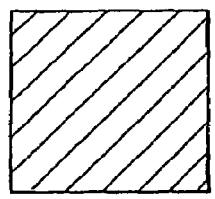
FIG. 16($a$) is a top view showing one example of the shape of the vibrating unit in the piezoelectric/electrostrictive actuator.
Figure 16B:
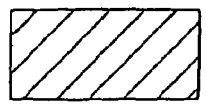
Figure 16C:
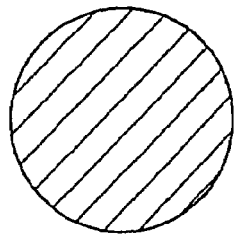
Figure 16D:
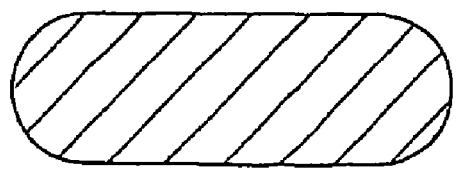
Figure 16E:
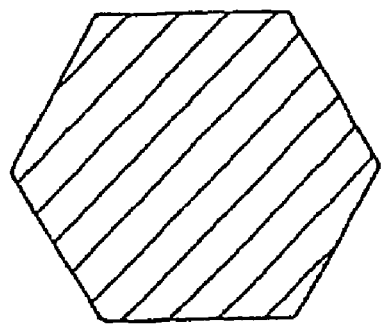

FIGS. 15(a) and 15(b) are perspective views showing examples of the base of the piezoelectric/electrostrictive actuator. In a piezoelectric/electrostrictive actuator 50 shown in FIG. 15(a), the vibrating unit 66 having the piezoelectric/electrostrictive operating unit 78 on one surface thereof may be supported by the supporting unit 68 to form the cavity 46, thereby forming a base 44. In a piezoelectric/electrostrictive actuator 51 shown in FIG. 15(b), the vibrating unit 66 having the piezoelectric/electrostrictive operating unit 78 on one surface thereof may be supported by the supporting unit 68 only on one side like the cantilever. The piezoelectric/electrostrictive actuator is not limited. However, the piezoelectric/electrostrictive actuator is a device having a piezoelectric/electrostrictive operating unit that causes the displacement on one surface of the vibrating unit, and has the piezoelectric/electrostrictive operating unit and the vibrating unit that are deformed. Therefore, when the large amount of displacement is required, preferably, another surface of the vibrating unit is not limited, that is, free, for the purpose of easy deformation. Further, when strong generating force and fast response are required, preferably, a structure for supporting both side of the piezoelectric/electrostrictive operating unit (refer to FIG. 15(a)) is used.

FIGS. 16(a) to 16(e) are top views showing examples of the shape of the vibrating unit 66. As viewed from the top of the vibrating unit 66, quadrate (FIG. 16(a)), rectangular (FIG. 16(b)), disc (FIG. 16(c)), elliptical (FIG. 16(d)), and hexagon (polygonal (FIG. 16(e)) shapes are shown. In the case of the disc vibrating unit 66 shown in FIG. 16(c), the entire circumference of the vibrating unit 66 may be supported by the supporting unit 68, or two facing portions or one portion on the circumference of the vibrating unit 66 may be supported by the supporting unit 68. As mentioned above, the piezoelectric/electrostrictive actuator does not limit the shape of the vibrating unit 66.

Next, a description is given of a manufacturing method of a piezoelectric/electrostrictive actuator, serving as the piezoelectric/electrostrictive actuator 20. The piezoelectric/electrostrictive actuator is manufactured by using a green sheet laminating method in the case of the base containing a ceramic material, and the piezoelectric/electrostrictive operating unit is manufactured by using a film forming method of a thin film or thick film.

The base 44 is manufactured as follows. A binder, a solvent, a dispersion agent, or a plasticizing material is added and mixed to ceramic particles of, e.g., zirconium oxide, thereby manufacturing slurry. The slurry is degassed and, thereafter, a green sheet with a predetermined thickness is manufactured by a reverse roll coater method or a doctor blade method. The shape for green sheet is variously processed by a method of punching using die and laser processing. A plurality of green sheets is sequentially laminated and then a ceramic green laminated-body is baked by pressure bonding with heat. The obtained green sheet laminated body is baked at a temperature of 1200 to 1600° C., thereby obtaining the base 44.

The piezoelectric/electrostrictive operating unit 78 is formed onto one surface of the base 44. The bottom electrode 77 is printed at a predetermined position of one surface of the base 44 by a film forming method, such as screen printing, and is baked at a temperature of 1250 to 1450° C. Next, the piezoelectric/electrostrictive element 79 is printed and is baked at a temperature of 1100 to 1350° C. Next, the top electrode 75 is printed at a temperature of, preferably, 500 to 900° C. Then, the piezoelectric/electrostrictive operating unit 78 is formed. After that, an electrode lead for connecting the electrode to a driving circuit is printed and is baked. By selecting a proper material, the electrodes of the piezoelectric/electrostrictive operating unit, the piezoelectric/electrostrictive element, and the electrode lead are sequentially printed, and are integrally baked once.

After forming the piezoelectric/electrostrictive actuator 20 as mentioned above, the piezoelectric/electrostrictive actuator 20 is polarized when the piezoelectric/electrostrictive actuator 20 needs the polarization. The polarization is performed by applying a voltage (polarization voltage) sufficiently higher than a driving voltage for use between the top electrode 75 and the bottom electrode 77. Although not limited, the polarization voltage is 70V when the driving voltage is 30V. In the piezoelectric/electrostrictive actuator 20, it is inspected to check whether or not the base 44 and the piezoelectric/electrostrictive operating unit 78 are normally manufactured. The base 44 and the piezoelectric/electrostrictive operating unit 78 are displaced or the vibrating unit 66 is undulated and, then, a desired amount of displacement is not obtained when the same (driving) voltage is applied between the electrodes.

Figure 4:
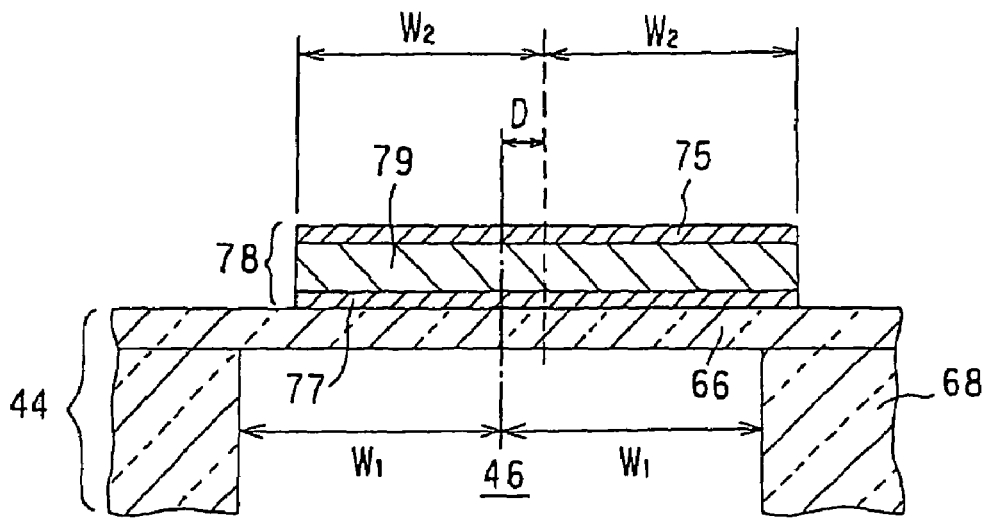
FIG. 4 is a cross-sectional view showing an example of the piezoelectric/electrostrictive actuator in which the piezoelectric/electrostrictive operating unit is deviated from a base, further showing a cross-section corresponding to FIG. 3.
Figure 13:
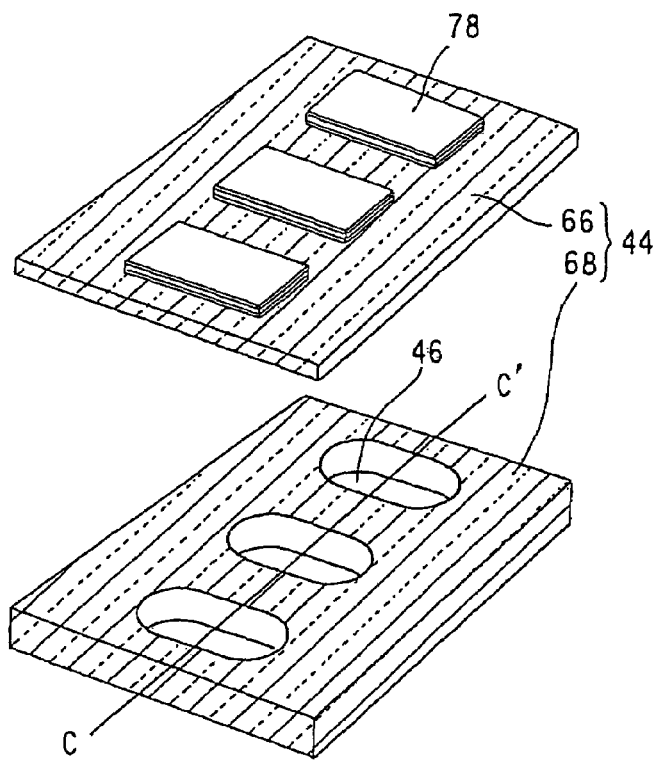
FIG. 13 is a perspective view showing one example of the piezoelectric/electrostrictive actuator, separating the vibrating unit and a supporting unit.
Figure 14:
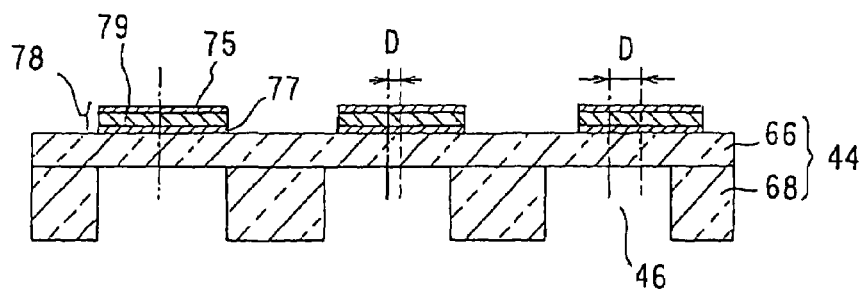
FIG. 14 is a cross-sectional view showing a CC' cross-section shown in FIG. 13.

FIG. 4 is a cross-sectional view showing an example of the piezoelectric/electrostrictive actuator in which the piezoelectric/electrostrictive operating unit 78 is laterally deviated from the base 44, further showing a cross-section corresponding to FIG. 3 indicating the piezoelectric/electrostrictive actuator without the lateral deviation is not caused. As mentioned above, some-degree lateral deviation as variation is necessarily caused in the manufacturing even under sufficient management. The lateral deviation is caused because the precision for positioning in the screen printing is limited and the extension is caused in screen photographing. A set of a plurality of the piezoelectric/electrostrictive actuators 20 shown in FIG. 3 is manufactured in many cases. Upon diving the set of the plurality of piezoelectric/electrostrictive actuator 20 into one and using the piezoelectric/electrostrictive actuator 20, a set of a plurality of piezoelectric/electrostrictive actuators 20 shown in FIG. 13 (although three piezoelectric/electrostrictive actuators 20 in FIG. 13, normally, several tens of piezoelectric/electrostrictive actuators 20 are used) is manufactured as shown in FIG. 13. In the screen printing, the bottom electrode 77, the piezoelectric/electrostrictive element 79, and the top electrode 75 are printed onto one surface of the base 44 having a plurality of cavities 46 with a conductive material paste and a piezoelectric/electrostrictive material paste. In this case, the above-mentioned reasons cause an uneven positional relationship between the base 44 (cavity 46) and the piezoelectric/electrostrictive element 79 in the entire piezoelectric/electrostrictive actuators 20, and the lateral deviation is caused. FIG. 14 is a cross-sectional view showing a CC' cross-section shown in FIG. 13, further showing an example of an uneven state of a plurality of piezoelectric/electrostrictive operating units. Referring to FIG. 14, the piezoelectric/electrostrictive operating unit 78 on the left side is not laterally deviated from the cavity 46, however, the piezoelectric/electrostrictive operating unit 78 in the center is slightly laterally deviated from the cavity 46, and the piezoelectric/electrostrictive operating unit 78 on the right is greatly laterally deviated from the cavity 46.

Figure 5:
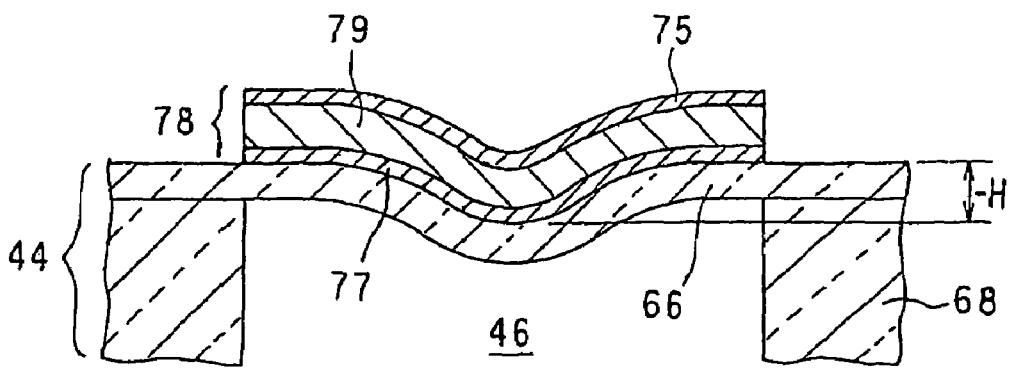
FIG. 5 is a cross-sectional view showing the piezoelectric electrostrictive actuator having the vibrating unit with undulation in the descending direction (in the drawing), further showing a cross-section corresponding to FIG. 3.

The dimension, serving as a prediction item in the inspection, of the piezoelectric/electrostrictive actuator 20, (serving as a structure having two or more elastic bodies), includes the above-mentioned amount of lateral deviation, that is, the amount of undulation of the vibrating unit 66 in the base 44 in addition to the amount of lateral deviation between the vibrating unit 66 in the base 44 (serving as the elastic body) and the piezoelectric/electrostrictive element 79 (serving as the elastic body) in the piezoelectric/electrostrictive operating unit 78. FIG. 5 is a cross-sectional view showing the piezoelectric/electrostrictive actuator having the vibrating unit 66 undulated downward in the drawing, corresponding to FIG. 3. In the specification, an amount H of undulation (refer to FIG. 5) has a positive amount of undulation, serving as upward undulation. That is, the piezoelectric/electrostrictive actuator shown in FIG. 5 is undulated with a negative amount H of undulation.

Figure 9:
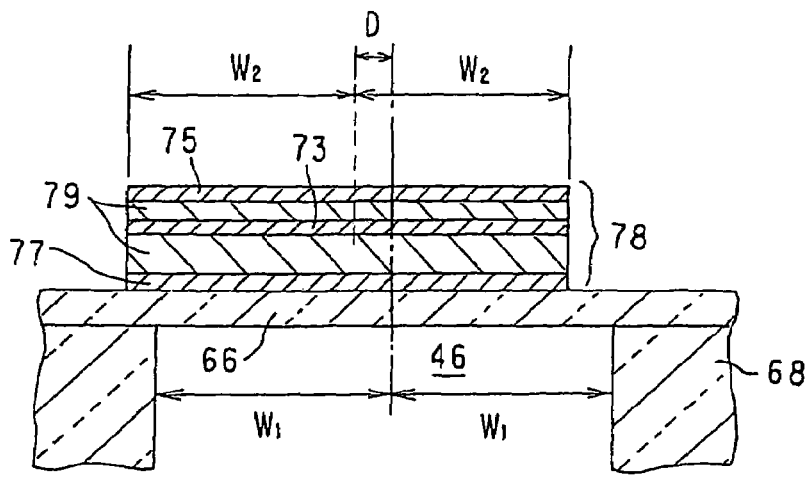
FIG. 9 is a cross-sectional view showing another example of the piezoelectric/electrostrictive actuator, further showing the piezoelectric/electrostrictive actuator having the lateral deviation by a distance D.
Figure 10:
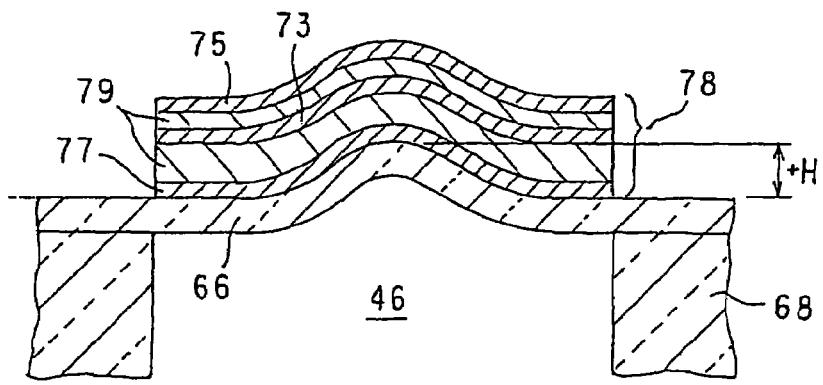
FIG. 10 is a cross-sectional view showing another example of the piezoelectric/electrostrictive actuator, further showing the piezoelectric/electrostrictive actuator having the undulation in the up direction with an amount H of undulation (in the drawing)
Figure 11:
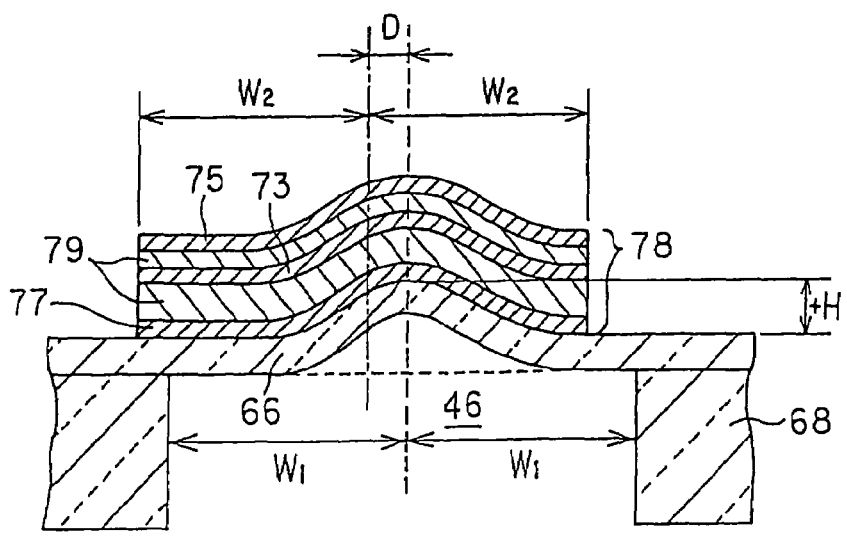
FIG. 11 is a cross-sectional view showing another example of the piezoelectric/electrostrictive actuator, further showing the piezoelectric/electrostrictive actuator having the lateral deviation by the distance D and the undulation in the up direction with the amount H of undulation (in the drawing)

Next, a description is given of the lateral deviation between the vibrating unit 66 and the piezoelectric/electrostrictive element 79 with reference to FIGS. 9 to 11. FIGS. 9 to 11 are cross-sectional views showing the cross sections corresponding to FIG. 3 including the vibrating unit and the piezoelectric/electrostrictive operating unit, further showing a piezoelectric/electrostrictive actuator having two layers of the piezoelectric/electrostrictive element 79. Referring to FIG. 9, the lateral deviation exists by a distance D (μm). Referring to FIG. 10, the undulation in the upward direction (in the drawing) exists with an amount H (μm) of undulation. Referring to FIG. 11, the upward undulation exists with the lateral deviation by the distance D (μm) and the upward undulation with the amount H (μm) of undulation. Referring to FIGS. 9 and 11, the amount of lateral deviation is changed (in other words, the distance D is changed), then, an area for overlapping the vibrating unit 66 and the piezoelectric/electrostrictive element 79 in the piezoelectric/electrostrictive operating unit 78, serving as a displacement generating unit, is changed, thereby changing the amount of displacement of the piezoelectric/electrostrictive actuator. In the piezoelectric/electrostrictive actuator, the length of the cavity on the BB' cross-section is much shorter than the length of the cavity on the AA' cross-section. The device property easily impacts the affection from the amount of lateral deviation on the BB' cross-section. In the specification, the amount of lateral deviation between the vibrating unit 66 and the piezoelectric/electrostrictive element 79 corresponds to the amount of deviation on the BB' cross-section shown in FIG. 1. The amount of lateral deviation shown in FIGS. 9 and 11 corresponds to the same one.

Figure 17A:
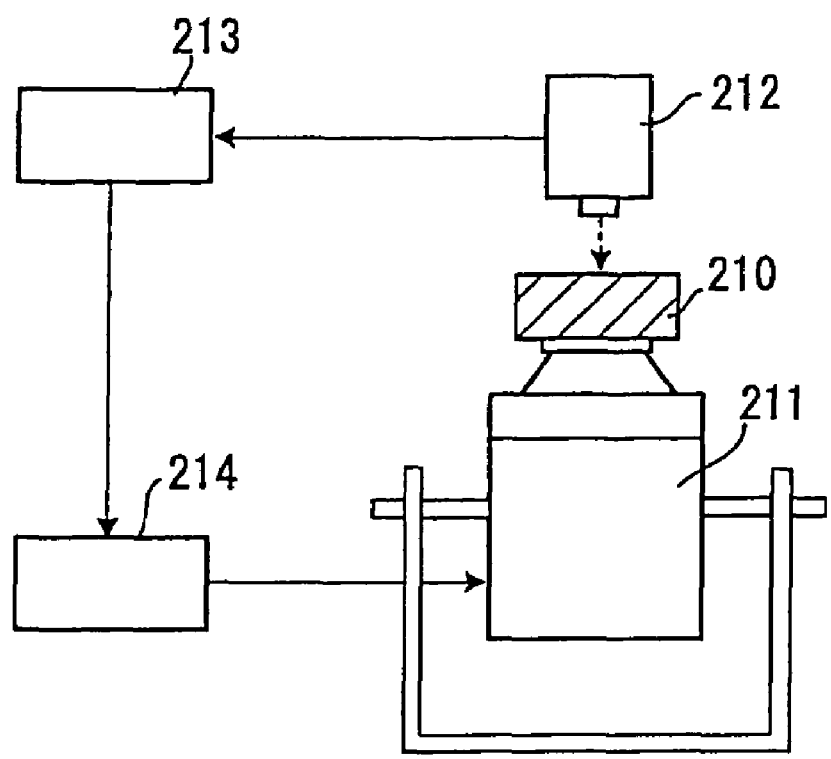
FIG. 17($a$) is a diagram showing the structure of one example of a frequency response characteristics measurement system.

Next, a description is given of an apparatus for vibrating the elastic body or the piezoelectric/electrostrictive device (piezoelectric/electrostrictive actuator or piezoelectric/electrostrictive sensor) and picking up the frequency response characteristics. FIG. 17(a) is a diagram showing the structure of a system for vibrating the elastic body or the piezoelectric/electrostrictive actuator by external force and picking up the frequency response characteristics. The frequency response characteristics measurement system mainly comprises: a vibration exciter 211; a laser vibration-meter 212; an FFT analyzer 213; and an amplifier 214. A piezoelectric/electrostrictive actuator 210 is fixed to the vibration exciter 211 by a two-sided tape or an adhesive and is vibrated. Then, the laser vibration-meter 212 measures the vibrations, the FFT analyzer 213 analyzes the vibrations and picks up the frequency response characteristics. The amplifier 214 amplifies a signal from the FFT analyzer 213 to drive the vibration exciter 211. In place of the FFT analyzer 213, a gain phase analyzer or a frequency analyzer can be used. Further, in place of the laser vibration-meter 212, an acceleration sensor can be used. The frequency response characteristics measurement system enables the vibration of any structure having two or more elastic bodies that is not a piezoelectric/electrostrictive device for generating vibrations by applying a voltage and that is not vibrated by electric force. Further, the frequency response characteristic is picked up and the dimension of the elastic body to the structure is predicted based on the frequency response characteristics.

Figure 17B:
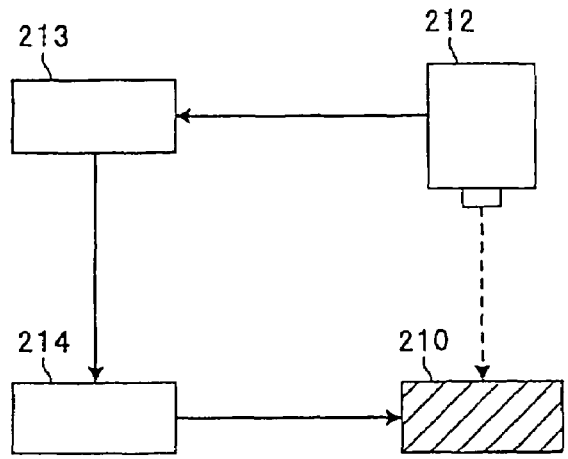

FIG. 17(b) is a diagram showing the structure of another example of the frequency response characteristics measurement system that directly drives the piezoelectric/electrostrictive actuator 210 without using the vibration exciter 211. Unlike the elastic body that is vibrated by itself, a piezoelectric/electrostrictive device including the piezoelectric/electrostrictive actuator has a function by which the piezoelectric/electrostrictive device itself is vibrated by inverse piezoelectric effect. Therefore, the piezoelectric/electrostrictive device is vibrated without the vibration exciter 211 shown in FIG. 17(a), and the measurement system of the frequency response characteristics is structured with low costs.

Preferably, the measurement systems of the frequency response characteristics shown in FIGS. 17(a) and 17(b) directly measure the mechanical vibration, and further measure the distribution of vibrations by changing a target point for laser irradiation or the install position of an acceleration sensor.

Figure 18:
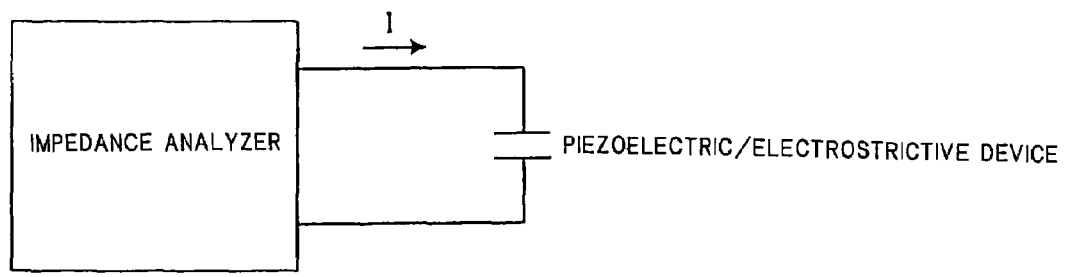
FIG. 18 is a diagram showing the structure of another example of the frequency response characteristics measurement system.

FIG. 18 is a diagram showing the structure of the measurement system of the frequency response characteristics that measures the impedance property, serving as one of the frequency properties of the piezoelectric/electrostrictive device. The frequency response characteristics measurement system shown in FIG. 18 measures the property between the impedance and the phase and the property between the admittance and the phase of the piezoelectric/electrostrictive device. Near the resonance frequency, the piezoelectric effect due to the increase in vibrations greatly changes the impedance of the piezoelectric/electrostrictive device and the resonant waveform is therefore obtained without using the laser vibration-meter. That is, unlike the frequency response characteristics measurement system shown in FIG. 17(a) or 17(b), the fast measurement is possible with low costs. Further, unlike the system using a network analyzer, the impedance measurement is possible with high precision.

Figure 19A:
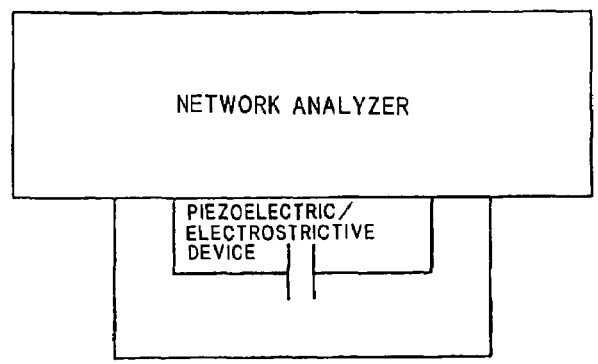
FIG. 19($a$) is a diagram showing the structure of one example of the frequency response characteristics measurement system.
Figure 19B:
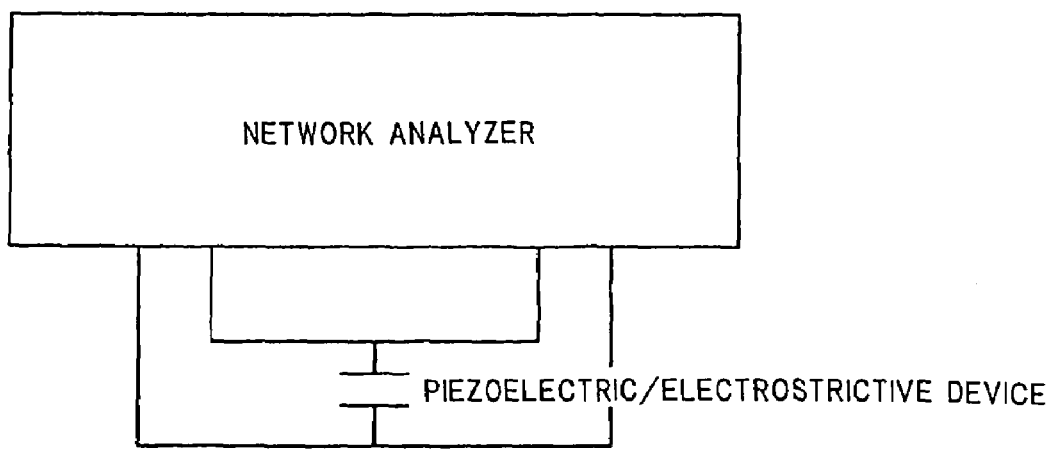

FIGS. 19(a) and 19(b) are diagrams showing the structures of examples of a measurement system of the frequency response characteristics of impedance (level and phase) by connecting a network analyzer to the piezoelectric/electrostrictive actuator, serving as an inspection target, via a probe (measurement jig) by analyzing transmission waves and reflection waves for an input signal. FIG. 19(a) shows an example of the frequency response characteristics measurement system using a transmitting method, and FIG. 19(b) is a diagram showing an example of the frequency response characteristics measurement system using a reflecting method. The frequency response characteristics measurement system enables the measurement of the frequency response characteristics, serving as the property between the gain and the phase, and further the measurement of the property between the impedance and the phase and the property between the admittance and the phase by using the function of the network analyzer. The frequency response characteristics measurement systems shown in FIGS. 19(a) and 19(b) enable the fast measurement with low costs, as compared with the frequency response characteristics measurement system shown in FIG. 18 using the impedance analyzer.

FIGS. 23, 24(a) to 24(c), and 25(a) to 25(c) are charts showing measurement examples of the property between the impedance and the phase (frequency response characteristics) of the piezoelectric/electrostrictive actuator using the transmitting method of the network analyzer. The method for inspecting the resonance frequency uses not only the minimum value and the maximum value of impedance and the minimum value and the maximum value of phase but also the minimum value and the maximum value of admittance and the minimum value and the maximum value of gain. A capacitance CP of the piezoelectric/electrostrictive element 79 is measured with an LCR meter by applying a voltage between the top electrode 75 and the bottom electrode 77. The applied voltage and frequency are not limited and may be 1V and 1 kHz, respectively.

Figure 20:
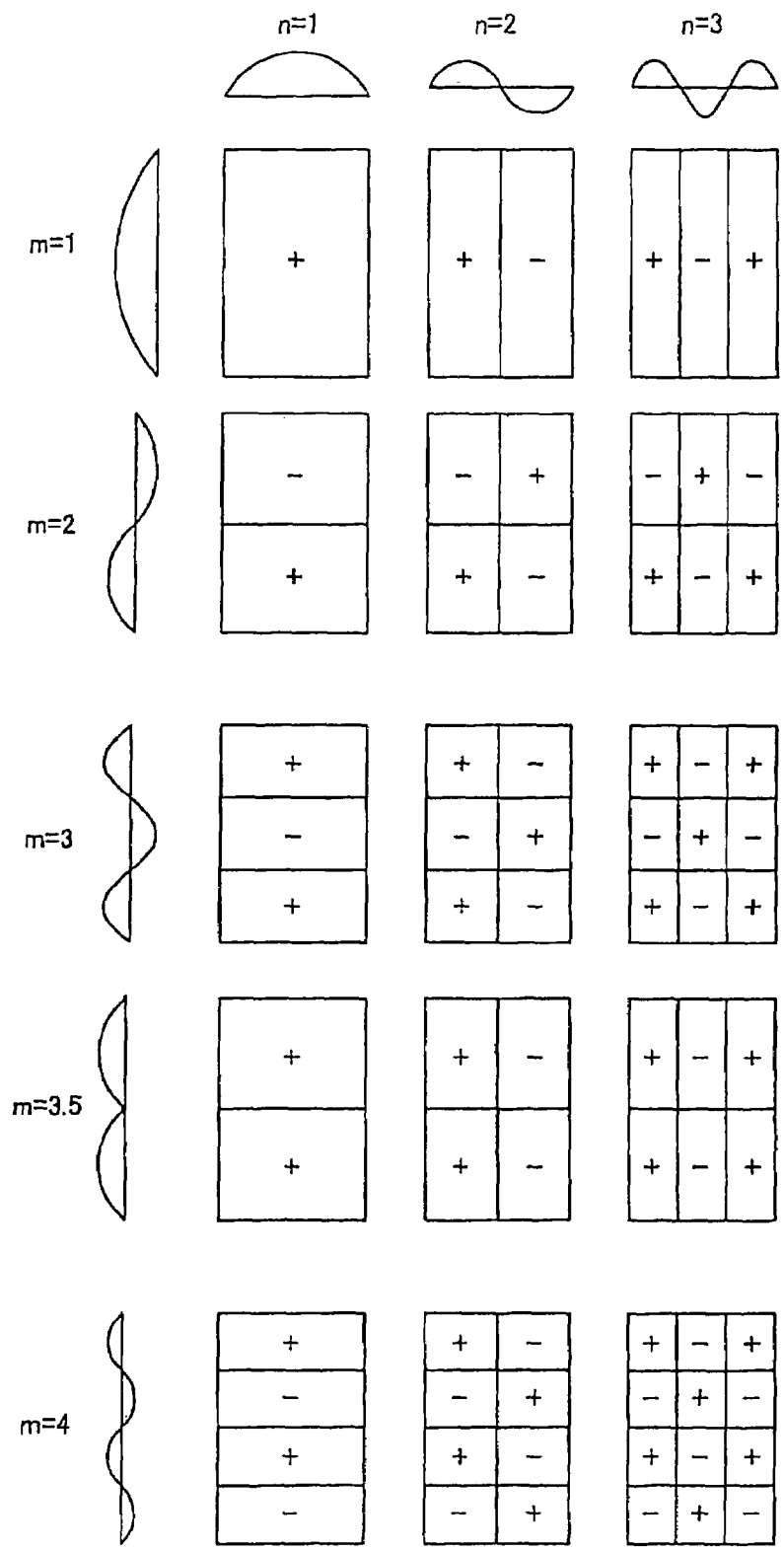
FIG. 20 is an explanatory diagram showing a vibrating mode of a rectangular plate.
Figure 21:
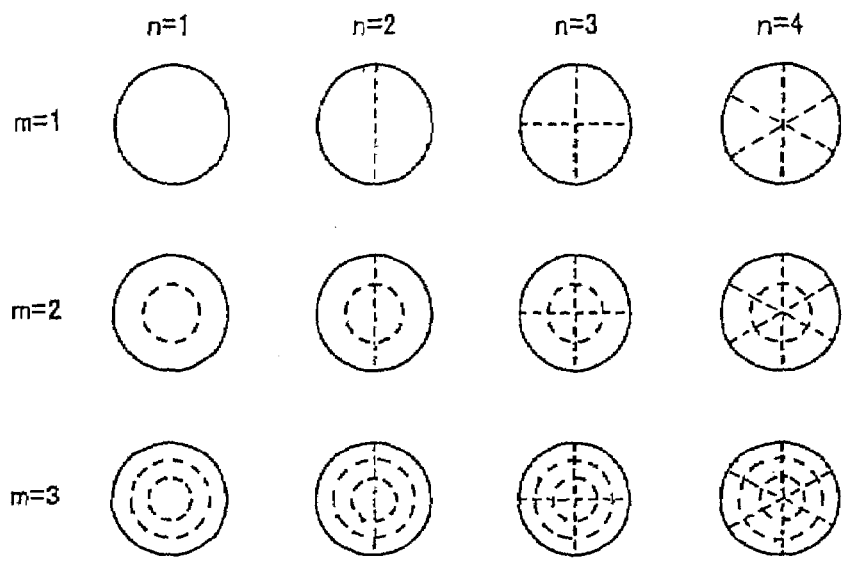
FIG. 21 is an explanatory diagram showing a vibrating mode of a disc plate.

Next, a description is given of a vibrating mode of a plate (plate member) in the resonance. As described above, generally, the vibration of plate is referred to as a vibrating mode of (m, n) degree. FIG. 20 is a diagram showing a vibrating mode of a rectangular plate. FIG. 21 is a diagram showing a vibrating mode of a disc plate. In place of the longitudinal direction and lateral direction of the rectangular plate, the vibrating mode is specified depending on the number of nodes in the circumferential direction and diameter direction of the disc plate, that is, the expression of (m, n).

In the vibrating mode of m other than 3.5 shown in FIG. 20, the direction of vibrations is opposite over the border, serving as the node. However, the present inventor finds out that the node exists in the center in the longitudinal direction and the vibrating mode on both sides of the center is single. The resonance frequency in the vibrating mode is intermediate between the vibrating mode of m (=3) and that of m (=4). Therefore, the degree m is 3.5 in the specification, and the vibrating mode of m (=3.5) is shown in FIG. 20. The generating reason of the vibrating mode is not completely found out. However, the vibrating mode is caused because of any one or both of the reason that the piezoelectric/electrostrictive operating unit exists on one surface of the vibrating unit (base) and the plate piezoelectric/electrostrictive actuator is not symmetrical in the up and down directions and the reason that the vibrating unit is minutely undulated in the and down directions.

Figure 22A:
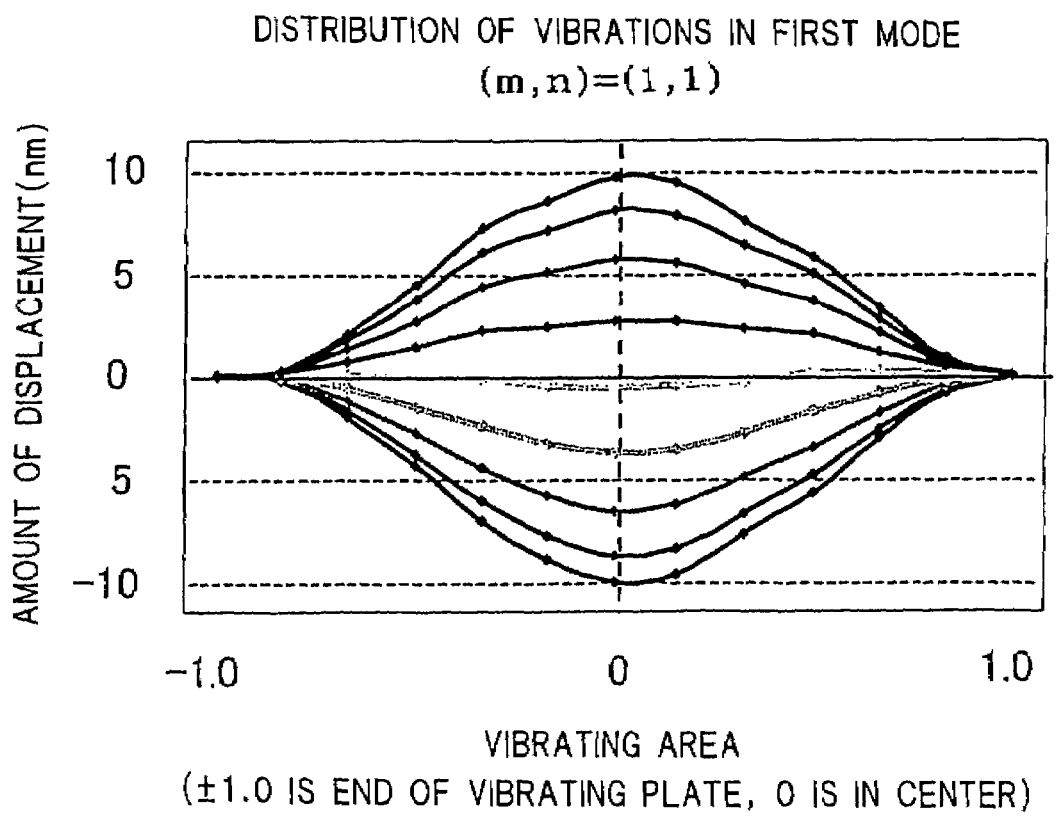
FIG. 22($a$) is a diagram showing the distribution of vibrations in a first vibrating mode.
Figure 22B:
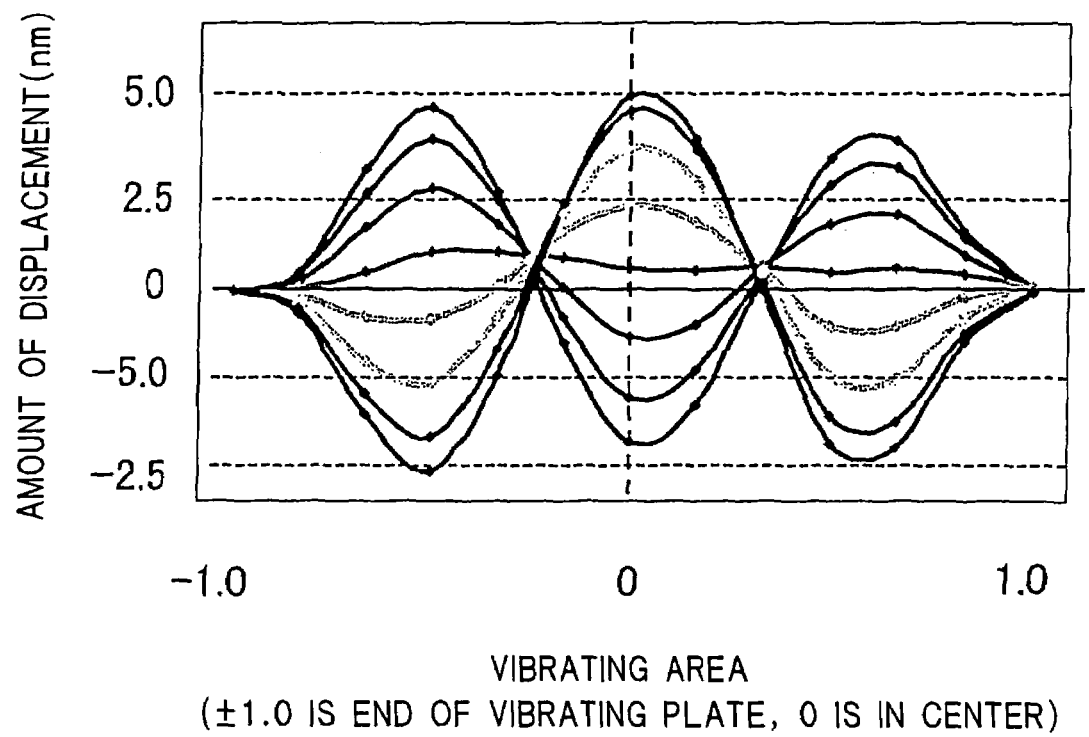
Figure 22C:
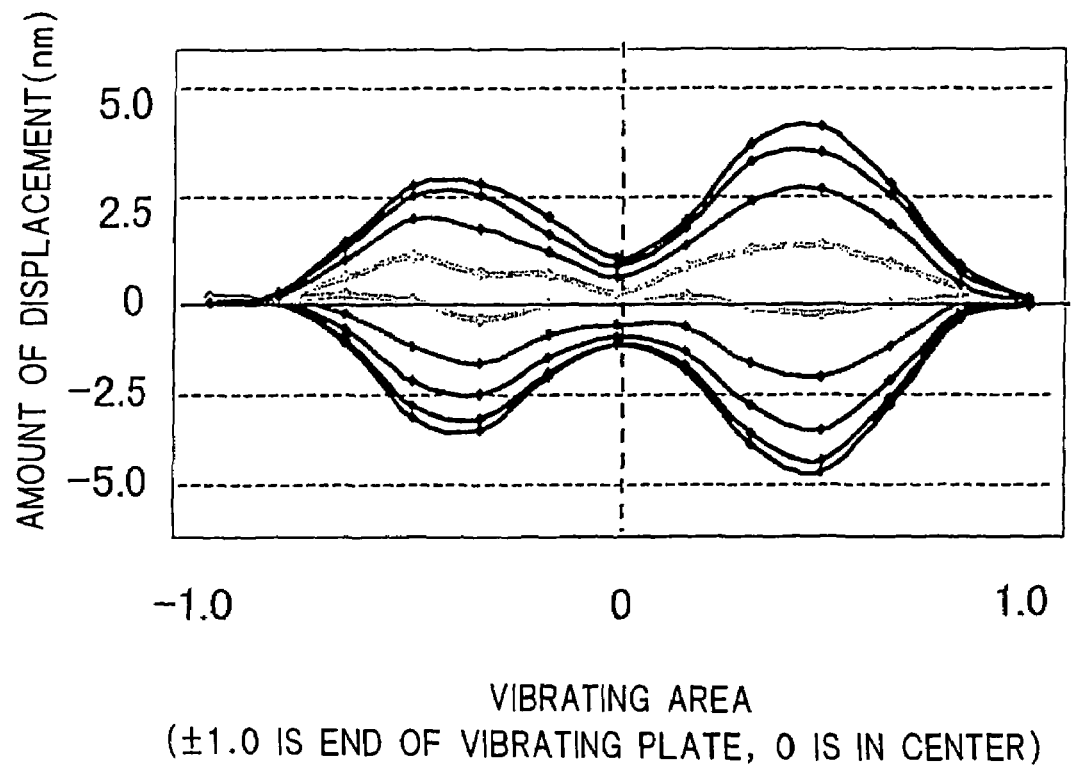

FIG. 22(a) is a diagram showing the distribution of vibrations in a vibrating mode of m (=1) and n (=1), corresponding to a vibrating area of the AA' cross-section of the piezoelectric/electrostrictive actuator shown in FIG. 1. Referring to FIG. 22(a), points of ±1.0 is supporting ones and a point of 0 is the center. FIG. 22(b) is a diagram showing the distribution of vibrations in a vibrating mode of m (=3) and n (=1). FIG. 22(c) is a diagram showing the distribution of vibrations in a vibrating mode of m (=3.5) and n (=1). In the frequency response characteristics measurement system shown in FIGS. 17(b) and 17(a), sine waves with a resonance frequency for specifying the vibrating mode vibrates the piezoelectric/electrostrictive actuator (plate member), the vibrations at a plurality of positions on the piezoelectric/electrostrictive actuator are measured by using a laser Doppler vibration-meter, and data on vibrations is totally analyzed and is observed by using animation, thereby measuring the distribution of vibrations and specifying the vibrating mode.

Figure 23:
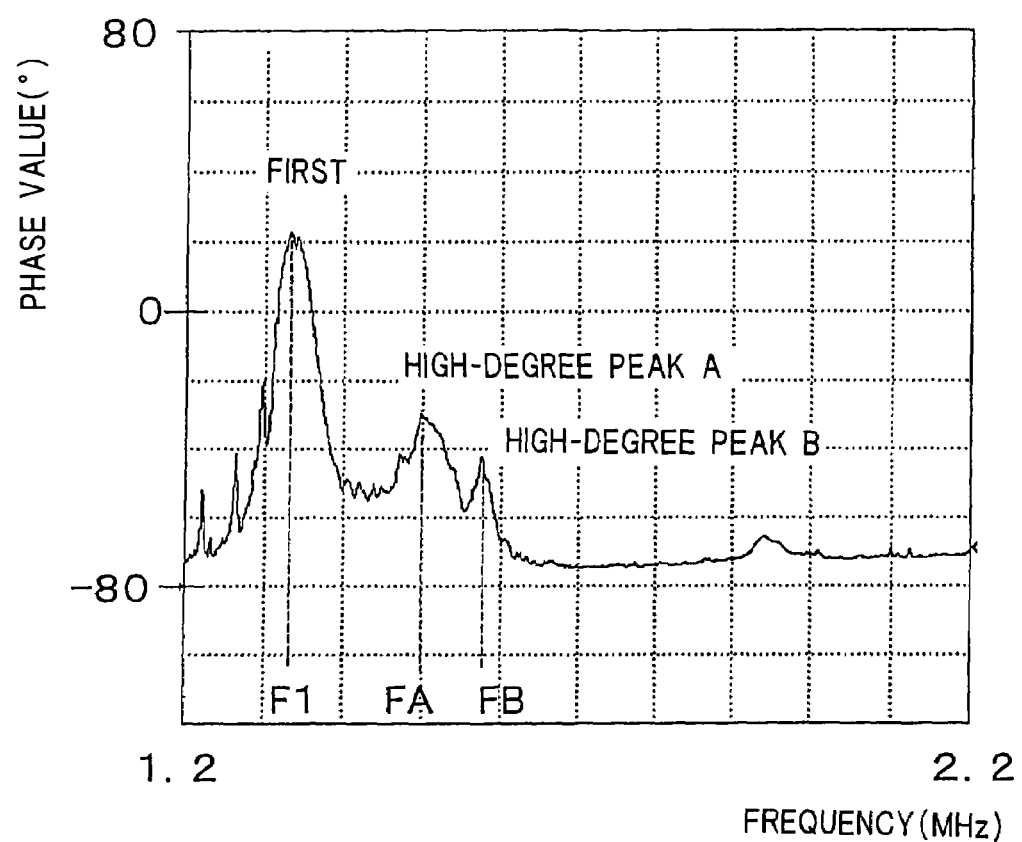
FIG. 23 is a chart showing one example of the frequency response characteristics of the piezoelectric/electrostrictive actuator.

Next, a specific description is given of the prediction method of the dimensional deviation and the amount of displacement based on the measurement data. FIG. 23 is a diagram showing one example of the frequency response characteristics of a phase value displayed on a screen of the network analyzer. A first resonance frequency F1 is detected as a frequency indicating the minimum value of the impedance of the lowest frequency and the maximum value of the phase. The first resonance frequency is in a vibrating mode of m (=1) and n (=1) shown in FIG. 22(a) (in the vibrations having one peak).

Sequentially, a resonance frequency FA with a high-degree peak A is detected as a frequency indicating a second-phase maximum value on the high-frequency side of the resonance frequency F1. The resonance frequency with the high-degree peak A is in a vibrating mode of m (=3) and n (=1) shown in FIG. 22(b) (in the vibrations having three peaks). In the example, the resonance frequency is generated at a frequency ratio FR1A that is equal to FA/F1, specifically, ranging 1.06 to 1.14.

Sequentially, a resonance frequency FB with a high-degree peak B is detected as a frequency indicating a third-phase maximum value on the higher-frequency side of the resonance frequency FA. The resonance frequency with the high-degree peak B is in a vibrating mode of m (=3.5) and n (=1) shown in FIG. 22(c) (in the vibrations having three peaks). In the example, the resonance frequency is generated at a frequency ratio FR1B that is equal to FB/F1, specifically, ranging 1.14 to 1.25.

Figure 26:
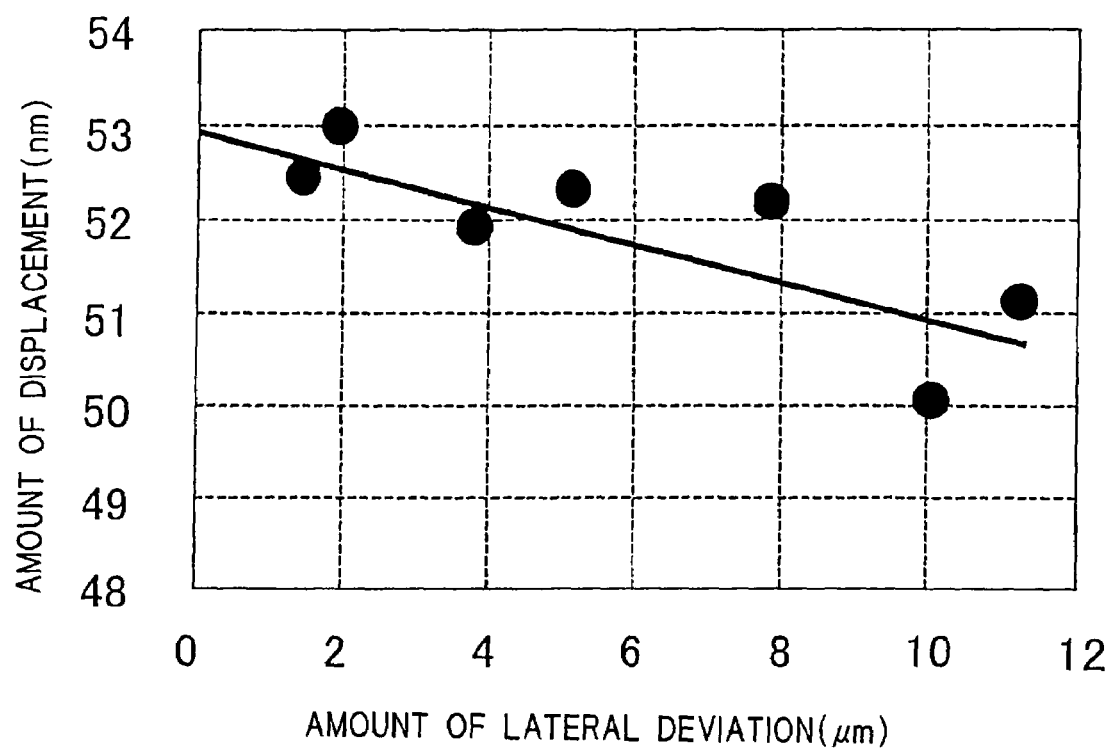
FIG. 26 is a graph showing a relationship between the amount of deviation between the piezoelectric/electrostrictive element and the vibrating unit in the piezoelectric/electrostrictive actuator and the amount of displacement of the piezoelectric/electrostrictive actuator having the amount of deviation.
Figure 27:
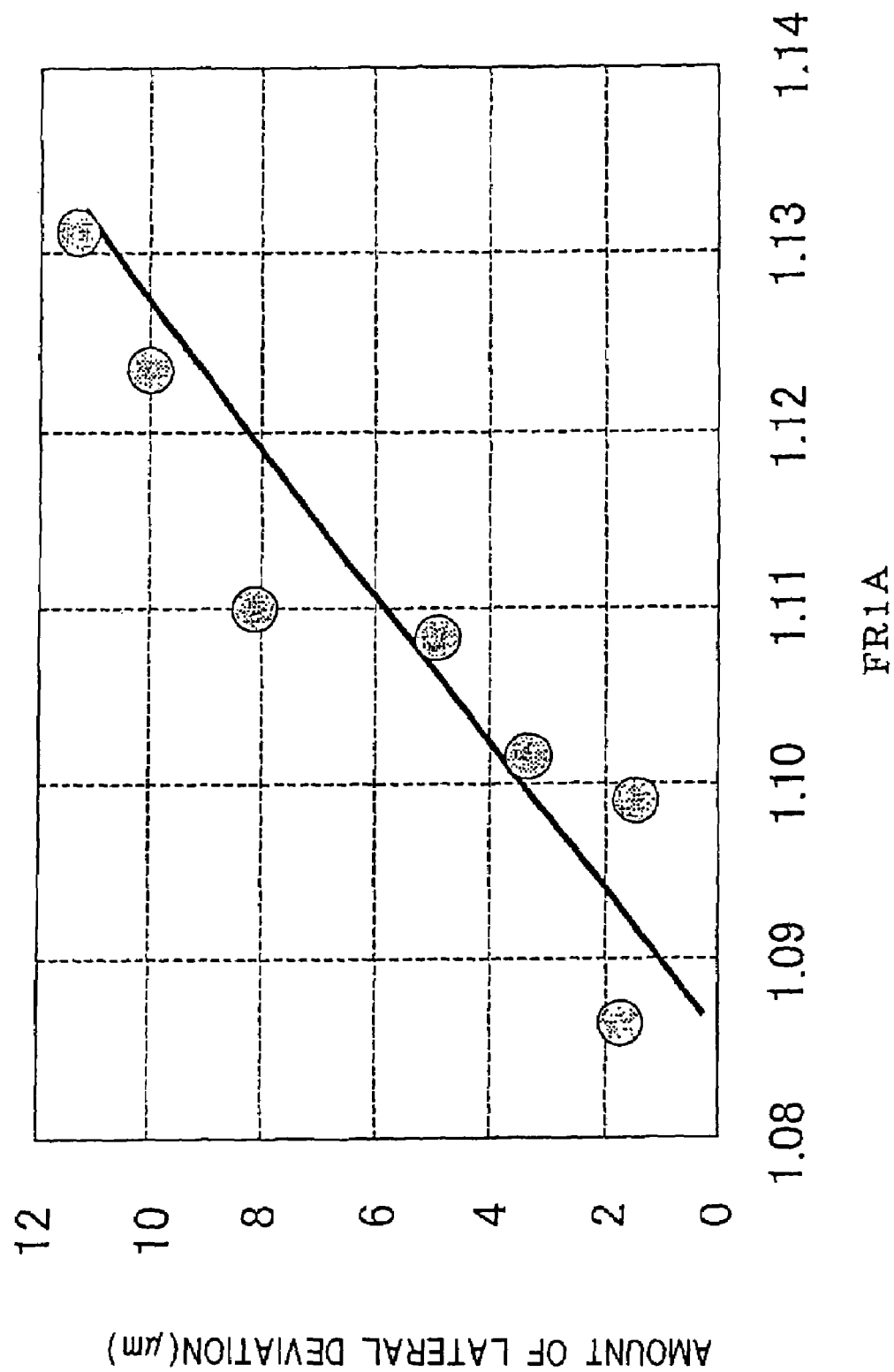
FIG. 27 is a graph showing a relationship between a frequency ratio FR1A and the amount of lateral deviation (absolute) between the piezoelectric/electrostrictive element and the vibrating unit.

FIG. 26 is a graph showing a relationship between the lateral deviation between the vibrating unit 66 and the piezoelectric/electrostrictive element 79 and the amount of displacement of the piezoelectric/electrostrictive actuator having the lateral deviation. For the purpose of clarifying the trend, the piezoelectric/electrostrictive actuator having the large amount of lateral deviation is analyzed. FIG. 27 is a graph showing a relationship between the frequency ratio FR1A (=FA/F1) and the amount of lateral deviation (absolute) between the vibrating unit 66 and the piezoelectric/electrostrictive element 79. As will be clearly understood with reference to FIG. 27, the frequency ratio FR1A is substantially proportional to the amount of lateral deviation (absolute) and the predicted amount of lateral deviation (dimension) is therefore obtained based on a value of a(FR1A) that is obtained by multiplying a coefficient "a" to the frequency ratio FR1A, as shown the following [Formula 10].

[Formula 10]

Predicted amount M10 of lateral deviation=a×FR1A+b (where a and b are coefficients).

Next, a description is given of the amount of undulation of the vibrating unit 66. Referring to FIG. 11, the amount of undulation is referred to as the height H(μm) to the top of the vibrating unit 66 extended from the plane connecting both ends of the vibrating unit 66. When the top of the vibrating unit 66 is caved from the plane connecting both the ends of the vibrating unit 66, the height H(μm) is expressed as a negative value.

Figure 29:
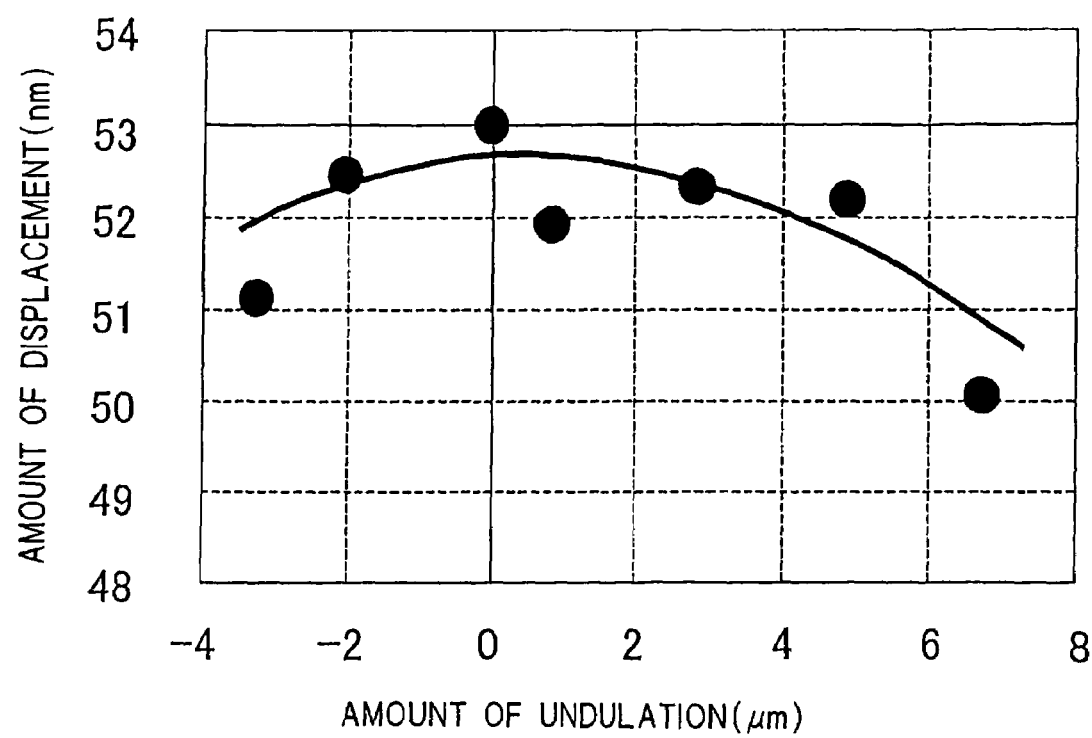
FIG. 29 is a graph showing a relationship between the amount of undulation of the vibrating unit in the piezoelectric/electrostrictive actuator and the amount of displacement of the piezoelectric/electrostrictive actuator having the amount of undulation.
Figure 30:
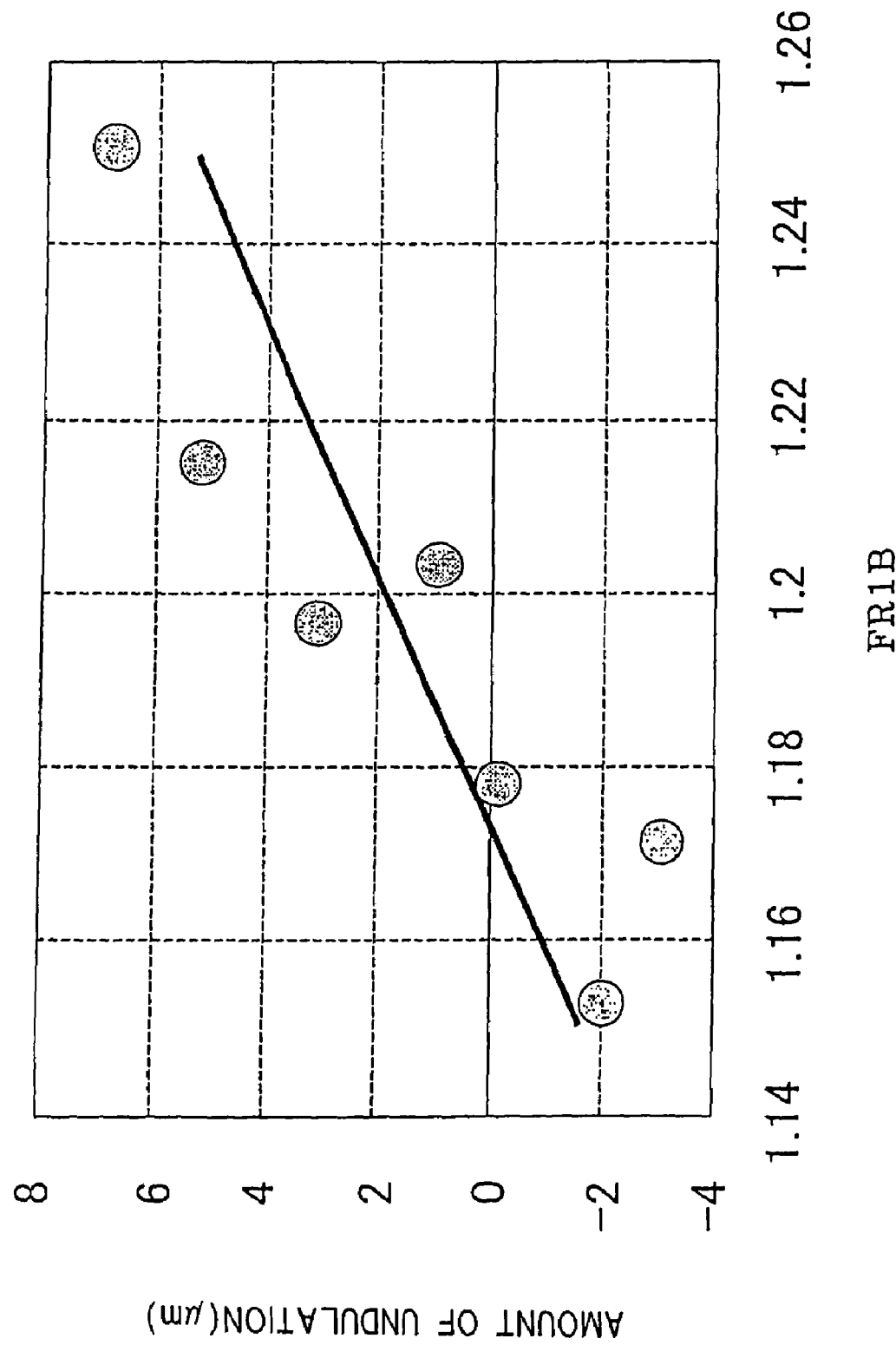
FIG. 30 is a graph showing a relationship between a frequency ratio FR1B and the amount of undulation of the vibrating unit in the piezoelectric/electrostrictive actuator.

FIG. 29 is a graph showing a relationship between the amount of undulation of the vibrating unit 66 and the amount of displacement of the piezoelectric/electrostrictive actuator having the amount of undulation. For the purpose of clarifying the trend, the piezoelectric/electrostrictive actuator having the large amount of undulation is analyzed. FIG. 30 is a graph showing a relationship between the frequency ratio FR1B (=FB/F1) and the amount of undulation of the vibrating unit 66. As will be clearly understood with reference to FIG. 30, the frequency ratio FR1B is substantially proportional to the amount of undulation and the prediction amount of undulation (dimension) is therefore obtained based on a value of a(FR1B) that is obtained by multiplying a coefficient "a" to the frequency ratio FR1B, as shown the following [Formula 11].

[Formula 11]

Predicted amount M11 of lateral deviation=a×FR1B+b (where a and b are coefficients).

Further, the amount of lateral deviation is substantially proportional to the amount of displacement, as will be clearly understood with reference to FIG. 26, and a relationship of a second polynominal expression is established between the amount of undulation and the amount of displacement, as will be clearly understood with reference to FIG. 29. Therefore, the predicted amount of displacement is obtained based on a value of a(FR1A) that is obtained by multiplying the coefficient "a" to the frequency ratio FR1A, a value of c(FR1B) that is obtained by multiplying a coefficient "c" to the frequency ratio FR1B, and a value of b(FR1B)$^2$ that is obtained by multiplying the coefficient "b" to square of FR1B (further, additionally using the capacitance CP), as expressed by the following [Formula 12]. In the manufacturing processing, upon forming the piezoelectric/electrostrictive element 79 by printing, the predicted amount of displacement is adjusted by minutely changing the printing position of the piezoelectric/electrostrictive element 79 so as to change the amount of lateral deviation between the vibrating unit 66 and the piezoelectric/electrostrictive element 79.

[Formula 12]

Predicted amount M12 of displacement=a×FR1A+b×(FR1B)$^2$+c×FR1B+d×CP+e (where a to e are coefficients).

Further, as expressed by the following [Formula 13], the predicted amount of displacement is obtained based on a value of e(F1) that is obtained by multiplying the coefficient "e" to the frequency ratio F1, a(FR1A) that is obtained by multiplying the coefficient "a" to the frequency ratio FR1A, a value of c(FR1B) that is obtained by multiplying the coefficient "c" to the frequency ratio FR1B, and a value of b(FR1B)$^2$ that is obtained by multiplying the coefficient "b" to the square of FR1B (further, additionally using the capacitance CP). In the manufacturing processing, upon forming the piezoelectric/electrostrictive element 79 by printing, the predicted amount of displacement is adjusted by minutely changing the printing position of the piezoelectric/electrostrictive element 79 so as to change the amount of lateral deviation between the vibrating unit 66 and the piezoelectric/electrostrictive element 79.

[Formula 13]

Predicted amount M13 of displacement=a×FR1A+b×(FR1B)$^2$+c×FR1B+d×CP+e×F1+f (where a to f are coefficients).

Figure 32A:
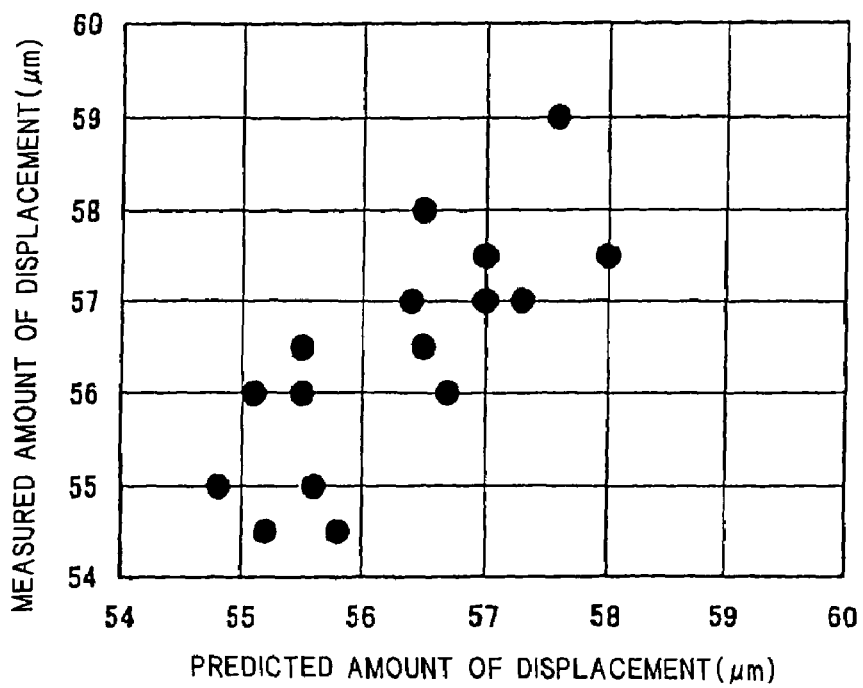
FIG. 32(a) is a graph showing the measured amount of displacement and the predicted amount of displacement upon predicting the amount of displacement by a first formula using only a capacitance CP.
Figure 32B:
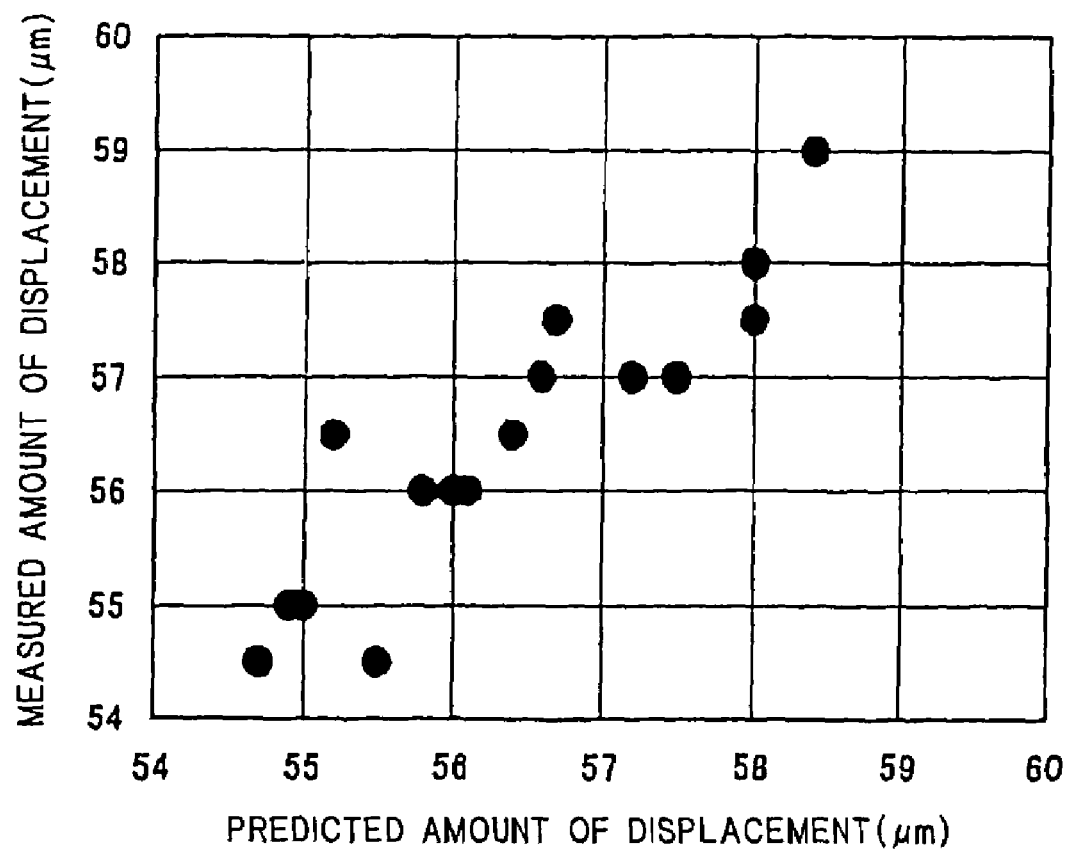
FIG. 32(b) is a graph showing the measured amount of displacement and the predicted amount of displacement upon predicting the amount of displacement using the frequency response characteristics.

FIG. 32(a) is a graph showing the measured amount of displacement and the predicted amount of displacement upon predicting the displacement based on a linear expression using only the capacitance CP (predicted amount of displacement=a×CP+b, where a and b are coefficients). FIG. 32(b) is a graph showing the measured amount of displacement and the predicted amount of displacement upon predicting the displacement based on [Formula 13]. The graph shown in FIG. 32(b) shows a substantially proportional relationship between the measured amount of displacement using the laser Doppler vibration-meter and the predicted amount of displacement of 16 piezoelectric/electrostrictive actuators that are manufactured with the same structure as that of the piezoelectric/electrostrictive actuator 20. As compared with the correlativity between the measured amount of displacement and the predicted amount of displacement shown in FIG. 32(a), the correlativity shown in FIG. 32(b) is preferable, that is, the displacement is predicted with high precision.

In the above-mentioned inspection, attention is paid to the resonance frequency and the resonant waveform of the vibrating modes of degrees (1, 1), (3, 1), and (3.5, 1). Further, the inspection is executed by paying attention to the resonance frequency and the resonant waveform in the vibrating mode other than those of degrees (1, 1), (3, 1), and (3.5, 1).

Figure 24A:
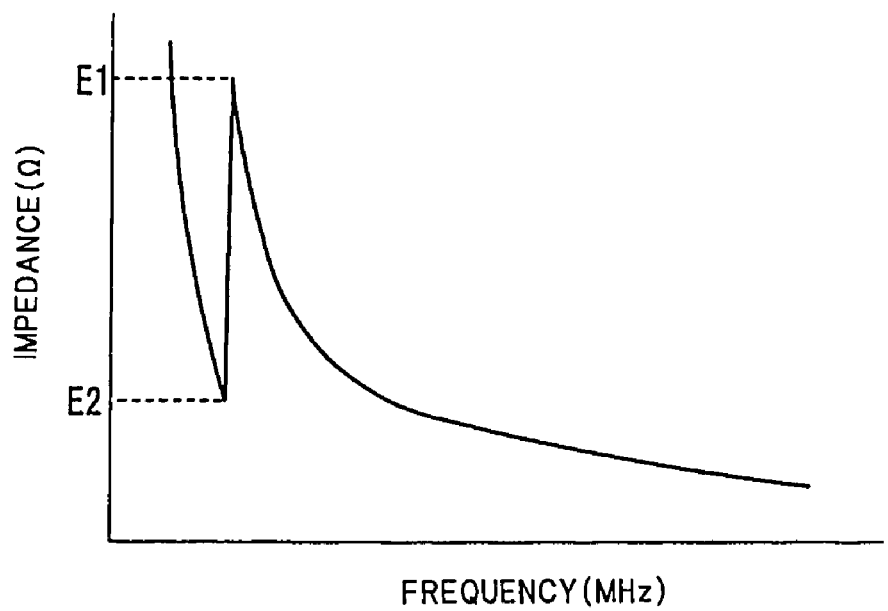
FIG. 24($a$) is a chart showing another example of the frequency response characteristics of the piezoelectric/electrostrictive actuator.
Figure 24A:
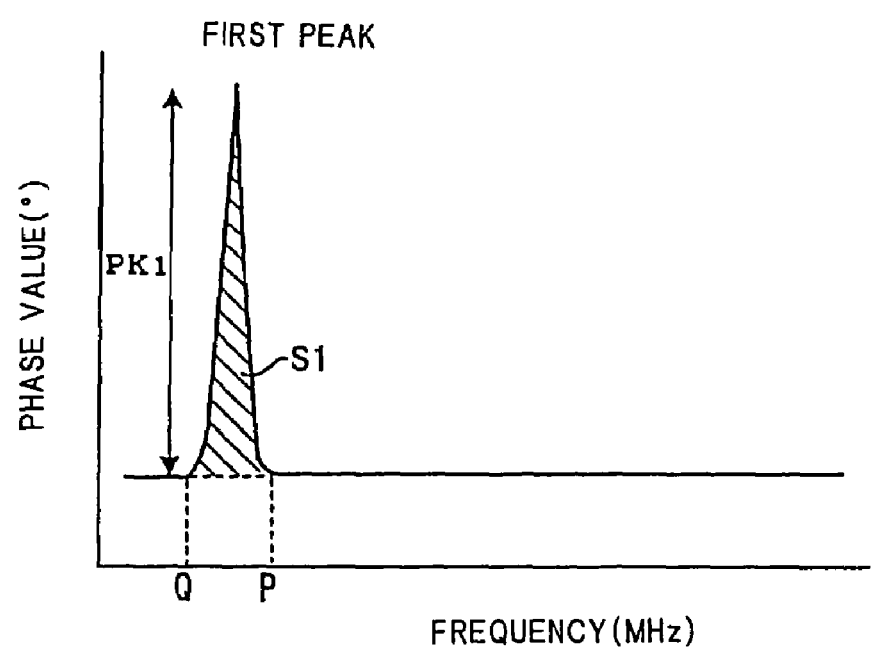
Figure 24B:
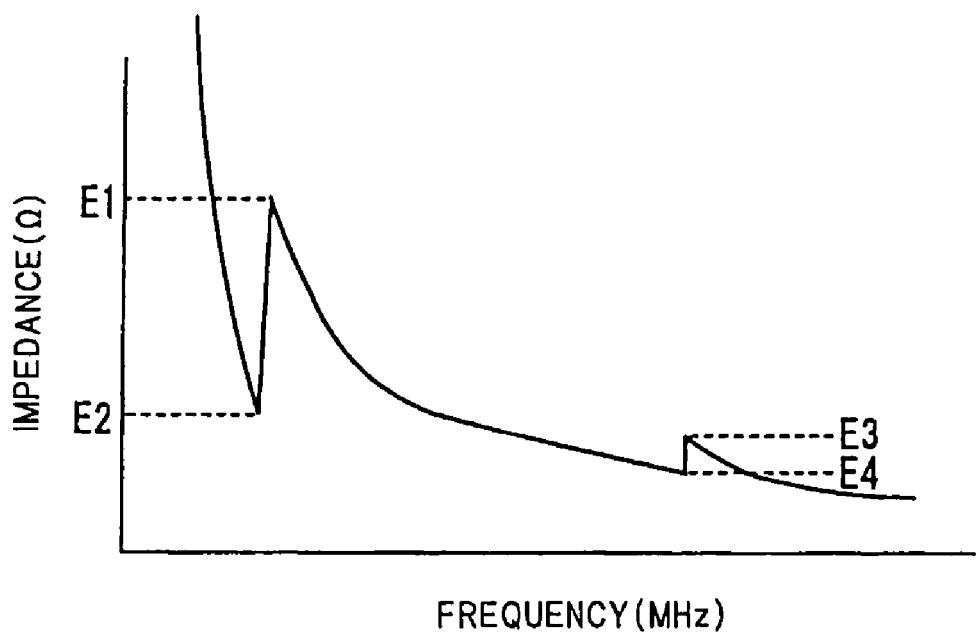
Figure 24B:
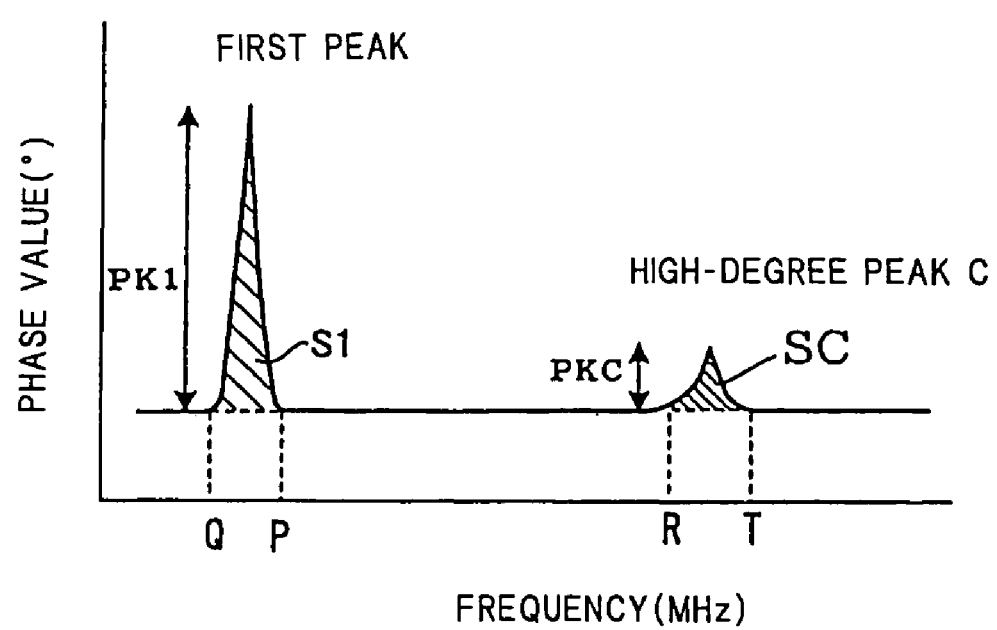
Figure 24C:
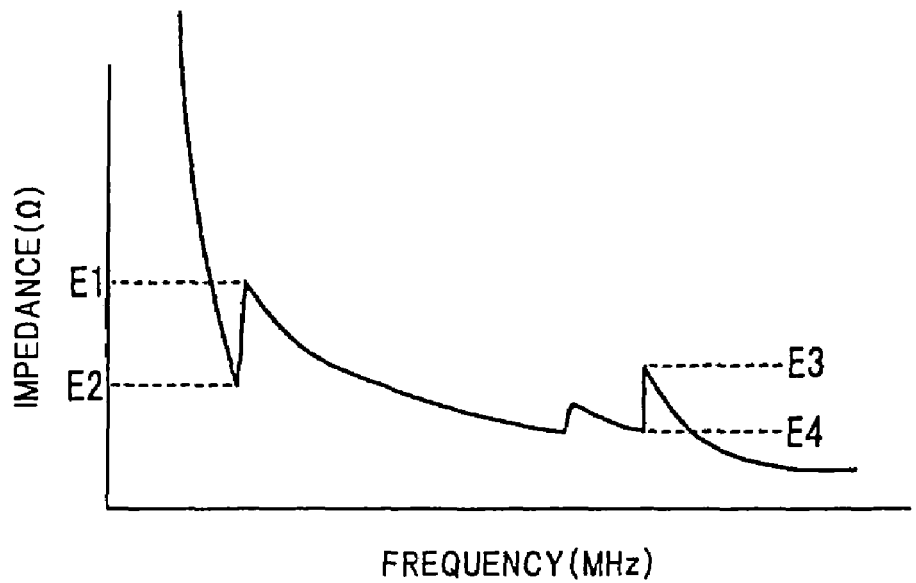
Figure 24C:
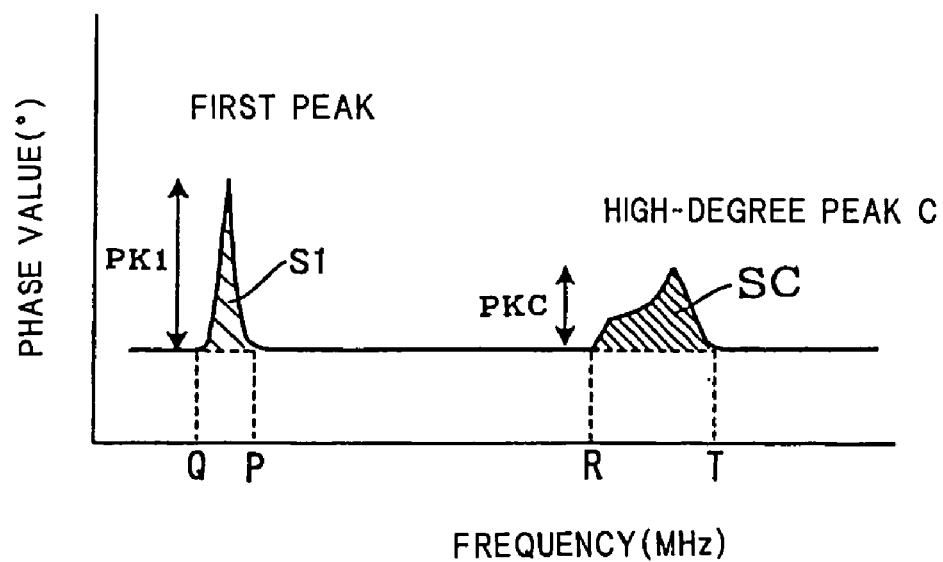
Figure 25A:
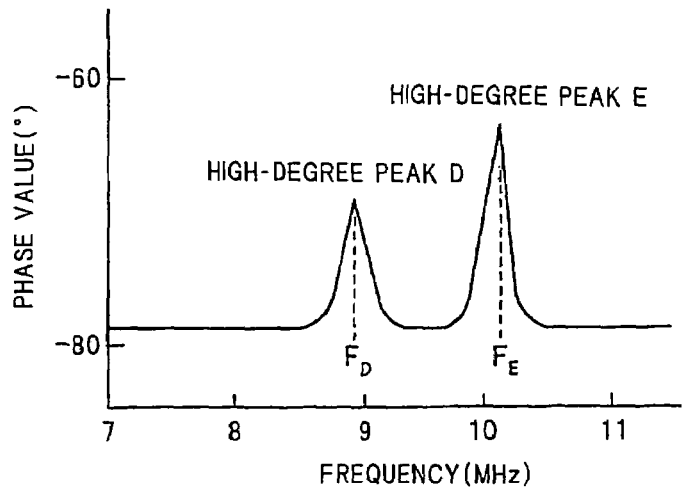
FIG. 25($a$) is a chart showing another example of the frequency response characteristics of the piezoelectric/electrostrictive actuator.
Figure 25B:
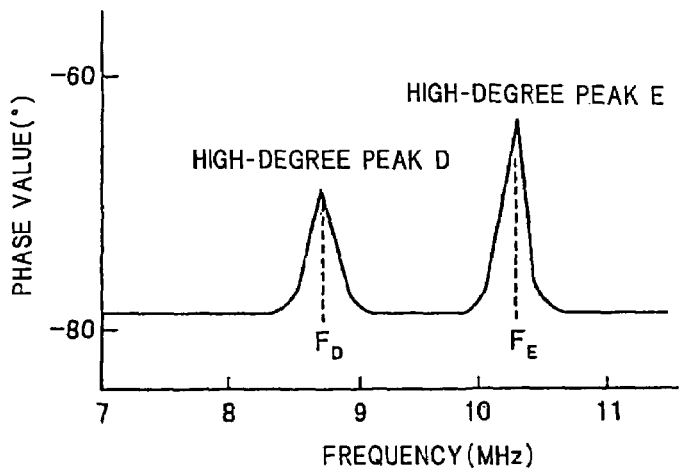
Figure 25C:
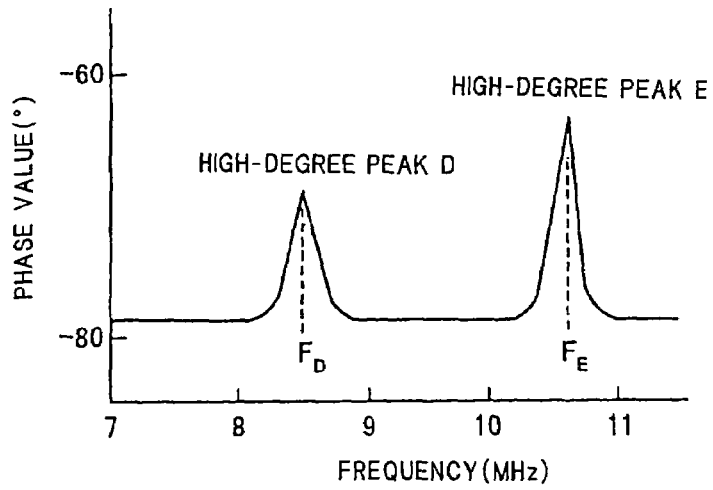

FIGS. 24(a) to 24(c) are charts showing measurement examples of the frequency properties to the impedance and the phase of the piezoelectric/electrostrictive actuator. FIG. 24(a) shows the frequency response characteristics without the amount of lateral deviation (when the amount of deviation is 0 μm), FIG. 24(b) shows the frequency response characteristics with a (relatively) small lateral deviation, and FIG. 24(c) shows the frequency response characteristics with a (relatively) large amount of lateral deviation. In the examples shown in FIGS. 24(a) to 24(c), the peak on the left in the drawings indicates the first peak, and the peak on the right in the drawings indicates a high-degree peak C. The first peak corresponds to the vibrating mode of (m, n) where m and n are 1, and the high-degree peak C corresponds to the vibrating mode of (m, n) where m and n are 1 and 2, respectively.

Referring to FIG. 24(a), in the piezoelectric/electrostrictive actuator without the lateral deviation, the peak of the resonance frequency in the vibrating mode of (1, 1) exists in the area with a low frequency and, however, a sharp peak does not exist in a predetermined area with a high frequency. Referring to FIGS. 24(b) and 24(c), in the piezoelectric/electrostrictive actuator with the lateral deviation, the peak of the resonance frequency (resonant waveform) in the vibrating mode of (1, 2) exists in the area with a high frequency (e.g., 4.5 to 5 MHz). As will be clarified on the comparison between FIGS. 24(b) and 24(c), the increase in amount of lateral deviation raises a peak height PKC and an area SC of the resonant waveform at frequencies R to T. Further, the increase in amount of lateral deviation reduces a peak height PK1 of the resonance frequency (resonant waveform) in the vibrating mode of (1, 1) in the area with a low frequency and an area S1 of the resonant waveform at frequencies Q to P.

The basic trend in the impedance is the same as that of the phase property. That is, referring to FIG. 24(a), in the piezoelectric/electrostrictive actuator without the lateral deviation, the difference between a maximum value E1 and a minimum value E2 generated by the resonance in the vibrating mode (1, 1) in the area with a low frequency is large, and a stepwise waveform does not exist in a predetermined area with a high frequency. Referring to FIGS. 24(*b*) and 24(*c*), in the piezoelectric/electrostrictive actuator with the lateral deviation, a stepwise waveform generated by the resonance in the vibrating mode (1, 2) exists in an area (e.g., 4.5 to 5 MHz) with a high frequency. As will be clarified on the comparison with reference to FIGS. 24(*b*) and 24(*c*), the increase in amount of lateral deviation raises the difference between a maximum value E3 and a minimum value E4.

Figure 28A:
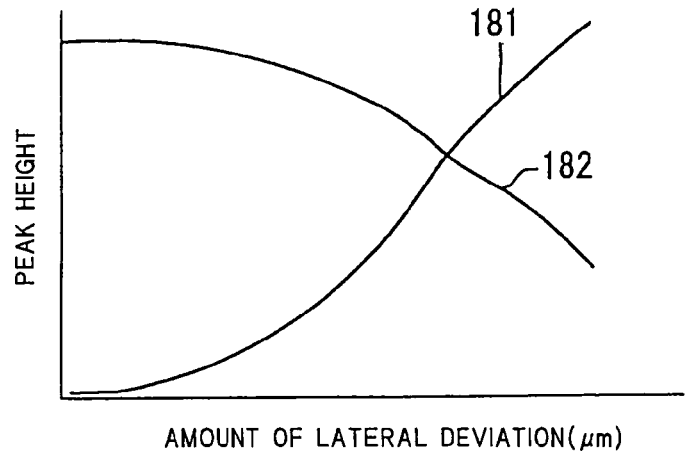
FIG. 28(a) is a graph showing a relationship between the amount of lateral deviation and a peak height (of a resonant waveform)
Figure 28B:
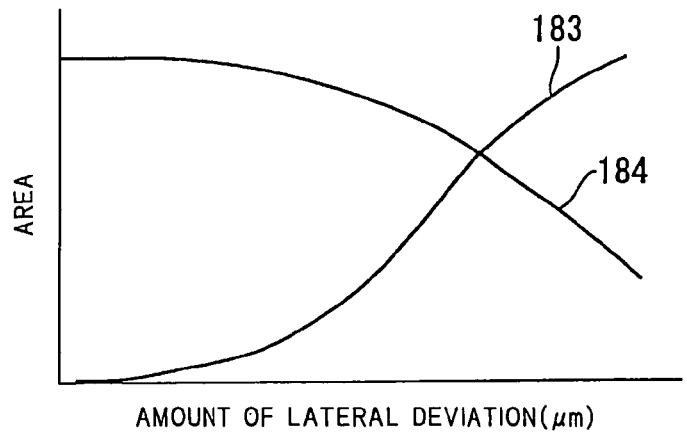
FIG. 28(b) is a graph showing a relationship between the amount of lateral deviation and an area (of the resonant waveform)
Figure 28C:
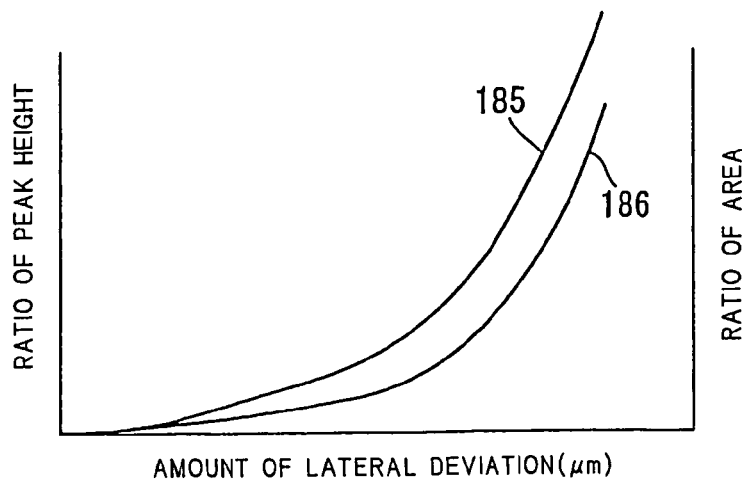
FIG. 28(c) is a graph showing a relationship between a ratio of the amount of lateral deviation and the area (of the resonant waveform) and a ratio of the amount of lateral deviation and the area (of the resonant waveform)

Referring to FIG. 28(*a*), a curve 181 denotes a relationship between the amount of lateral deviation and the height PKC of the high-degree peak C, and a curve 182 denotes a relationship between the amount of lateral deviation and the height PK1 of the first peak. Referring to FIG. 28(*b*), a curve 183 denotes a relationship between the amount of lateral deviation and an area SC of the high-degree peak C, and a curve 184 denotes a relationship between the amount of lateral deviation and an area S1 of the first peak. Referring to FIG. 28(*c*), a curve 185 denotes a relationship between the amount of lateral deviation and a peak-height ratio PKC/PK1, and a curve 186 denotes a relationship between the amount of lateral deviation and an area ratio SC/S1 of peak. As will be clarified with reference to FIGS. 28(*a*) to 28(*c*), the small amount of lateral deviation increases the peak height PKC and the area SC (that is, detecting sensitivity is high), and the large amount of lateral deviation increases the height ratio PKC/PK1 of peak and the area ratio SC/S1 (detecting sensitivity is high).

A description is given of phenomena of the increase in peak height (waveform) in the vibrating mode (1, 2) due to the lateral deviation with the following reasons. That is, the piezoelectric/electrostrictive operating unit is arranged to the vibrating unit without the lateral deviation, the center of gravity of the piezoelectric/electrostrictive actuator, serving as a structure, matches the center of vibrations. Further, the expansion and contraction of the piezoelectric/electrostrictive operating unit excites the bending displacement that is originally approximate to the vibrating mode (1, 1). That is, the displacement of the center of the vibrating unit is greatly excited. In this case, the excitation is relatively easy in the odd-degree vibrating modes (3, 1), (5, 1), (7, 1), and (1, 3) in which the center of the vibrating unit is greatly vibrated and, however, the excitation is not observed in the even-degree vibrating modes (2, 1), (4, 1), and (1, 2) in which the center of the vibrating unit corresponds to the node. Actually, in the vibrating mode (1, 2) shown in FIG. 24(*a*), the excitation is not observed. On the contrary, when the piezoelectric/electrostrictive operating unit is arranged to the vibrating unit with the lateral deviation, the center of vibrations is deviated from the center of gravity of the piezoelectric/electrostrictive actuator and the even-degree vibrating mode is excited. The increase in lateral deviation raises the even degree of the vibrating mode. The lateral deviation that exerts a great influence is positional deviation on the BB' cross-section of the piezoelectric/electrostrictive actuator shown in FIG. 1, and the vibrating mode (1, 2) (refer to FIG. 20) with the node in the center of the lateral direction with a narrow width is greatly excited. In the positional deviation on the AA' cross-section shown in FIG. 1, the vibrating mode (2, 1) is greatly excited, the positional deviation in this direction does not exert a disadvantageous influence on the displacement and, thus, is not described in the specification. This consideration can be applied to the inspection of dimensional deviation. As compared with a prediction method using the high-degree peak A shown in FIG. 23, preferably, the number of peaks (resonant waveforms), serving as noise, near the peak (resonant waveforms) is relatively small, the possibility for erroneously detecting another undesired peak (resonant waveform) is low, and the lateral deviation is predicted with high detecting sensitivity and high precision. A prediction formula of the amount of lateral deviation due to the high-degree peak C is approximately a straight line near the origin in FIG. 28(*a*) and is therefore simply expressed by the following [Formula 14].

[Formula 14]

Predicted amount M14 of lateral deviation=a×PKC (where a is coefficient).

Figure 31:
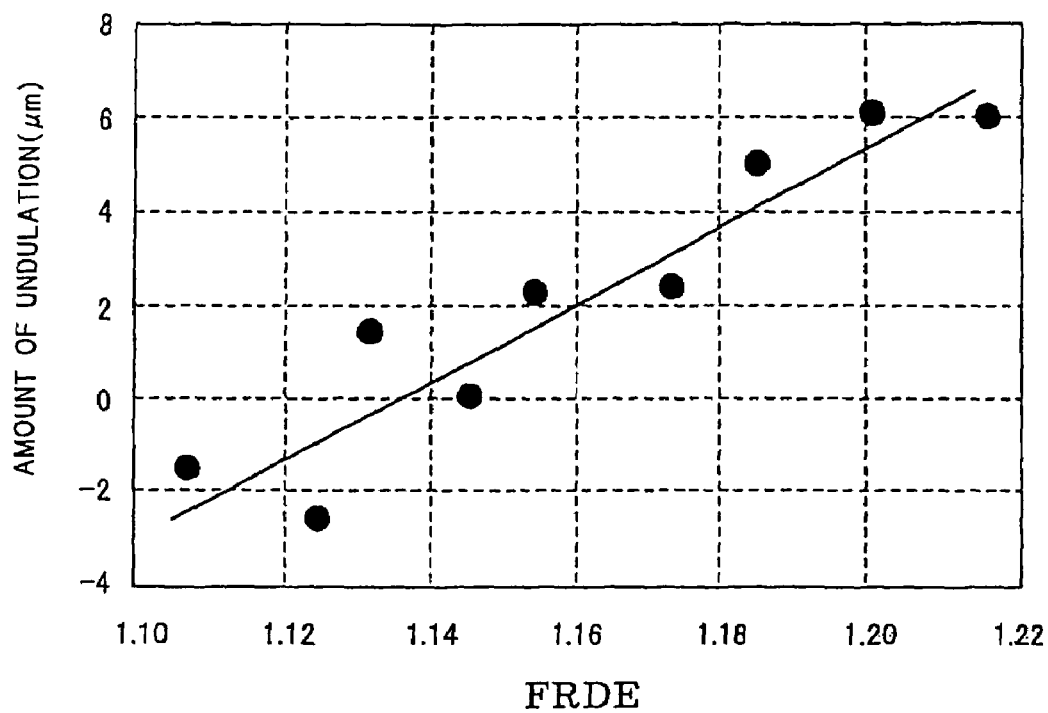
FIG. 31 is a graph showing a relationship between a frequency ratio FRDE and the amount of undulation of the vibrating unit in the piezoelectric/electrostrictive actuator.

FIGS. 25(*a*) to 25(*c*) are diagrams showing examples of the frequency response characteristics of a phase value displayed on the screen of the network analyzer, FIG. 25(*a*) shows the frequency response characteristics of the piezoelectric/electrostrictive actuator (refer to FIG. 5) having the vibrating unit with the downward undulation, FIG. 25(*b*) shows the frequency response characteristics of the piezoelectric/electrostrictive actuator (refer to FIG. 3) having the vibrating unit without the downward undulation, and FIG. 25(*c*) shows the frequency response characteristics of the piezoelectric/electrostrictive actuator (refer to FIG. 10) having the vibrating unit with the upward undulation. Referring to FIGS. 25(*a*) to 25*a*(*c*), a resonance frequency FD of a high-degree peak D is detected at a frequency ranging 8 to 9 MHz, and a resonance frequency FE of a high-degree peak E is detected at a frequency ranging 10 to 11 MHz. The resonance frequency of the high-degree peak D is one in the vibrating mode (1, 3), and the resonance frequency of the high-degree peak E is one in the vibrating mode (3.5, 3). A frequency ratio FRDE (=FE/FD) of the two resonant frequencies is relative to the amount of undulation of the piezoelectric/electrostrictive actuator, the amount of undulation of the piezoelectric/electrostrictive actuator is predicted by obtaining the frequency ratio FRDE of the resonant frequencies FE and FD. That is, although the frequency ratio FRDE is slightly shifted, the amount of undulation and the amount of displacement are predicted based on the similar calculating formula to the frequency ratio FR1B. As compared with the method using the first peak and the high-degree peak B shown in FIG. 23, according to the prediction method of the amount of undulation using the high-degree peak D and the high-degree peak E shown in FIGS. 25(*a*) to 25(*c*), the number of peaks (resonant waveforms), serving as noise, is relatively small near the peak (resonant waveform) and another peak is erroneously detected with low possibility. Therefore, preferably, the amount of undulation is predicted with high sensitivity and high precision. FIG. 31 is a graph showing a relationship between the frequency ratio FRDE and the amount of undulation of the vibrating unit in the piezoelectric/electrostrictive actuator. Since a predetermined formula of the amount of undulation using the high-degree peaks D and E is approximately a straight line near the origin in FIG. 31 and is therefore simply expressed by the following [Formula 15].

[Formula 15]

Predicted amount M15 of undulation=a×FRDE+b (where a and b are coefficients).

Further, the predicted amount of displacement is expressed by the following [Formula 16] in consideration of the prediction formula of the amount of displacement using the high-degree peaks C, D, and E, serving as a quadratic curve of the amount of undulation and the amount of displacement.

[Formula 16]

Predicted amount M16 of displacement=a×PKC+b×(FRDE)$^2$; +c×FRDE+d×CP+e×F1+f (where a to f are coefficients).

It is determined, based on the predicted amount of lateral deviation, predicted amount of undulation, and predicted amount of displacement that are obtained, whether or not the produced piezoelectric/electrostrictive actuator 20 is a defective product and the inspection then ends. After that, only the piezoelectric/electrostrictive actuator 20 that passes through the inspection is shipped.

Conventionally, since the piezoelectric/electrostrictive actuator is inspected only based on the capacitance of the piezoelectric/electrostrictive element, the inspection result does not reflect the difference in products of the base comprising another component forming the piezoelectric/electrostrictive actuator, that is, the vibrating unit and the supporting unit. Therefore, the improvement in inspection precision is limited. However, the inspection result is obtained by actually vibrating the piezoelectric/electrostrictive actuator having the results of the predicted amount of lateral deviation, predicted amount of undulation, and predicted amount of displacement. The inspection result including the predicted amount of lateral deviation, predicted amount of undulation, and predicted amount of displacement reflects the entire components forming the piezoelectric/electrostrictive actuator (including any non-predicted component). Thus, the variations in dimension and the amount of displacement are certainly identified, the inspection precision is higher than that of the conventional inspection, and it is accurately determined whether or not the produced piezoelectric/electrostrictive actuator is a defective product. Since only the manufactured piezoelectric/electrostrictive actuator is vibrated without the destruction and dissolution of the piezoelectric/electrostrictive actuator, a long inspection time is not required. A micro switch in which the non-defective piezoelectric/electrostrictive actuator passing through the inspection is used as an actuator unit, the amount of displacement of the vibrating unit is converged within a predetermined range and the variation in switch operation is suppressed.

Similarly to the amount of displacement of the piezoelectric/electrostrictive actuator, the dimension, such as the amount of deviation and the amount of undulation, exerts a great influence on the detecting sensitivity of the piezoelectric/electrostrictive sensor. That is, the multiple classification analysis is performed by using the capacitance, the resonance frequency, and the ratio of resonance frequency in the piezoelectric/electrostrictive sensor, thereby predicting and estimating the detecting sensitivity with high precision.

Further, the present invention is effectively applied to the inspection of a set of a plurality of piezoelectric/electrostrictive actuators arranged in the vertical and horizontal directions. That is, the variation in properties of the set of piezoelectric/electrostrictive actuators corresponds to the variation in dimensional deviations of the piezoelectric/electrostrictive actuators in the set of piezoelectric/electrostrictive actuators. In order to improve the quality of the piezoelectric/electrostrictive actuator, when the level of variation is selected by inspecting the variation in dimensional deviation and the piezoelectric/electrostrictive actuator is used for applications, it is possible to precisely predict the variation in properties of the set of piezoelectric/electrostrictive actuators by using the information including the resonant frequencies, the ratio of resonant frequencies, the peak height of resonant waveform, and the area in the first and high-degree vibrating modes.

Next, a description is given of a dimension predicting program of an elastic body and a prediction program of the amount of displacement of the piezoelectric/electrostrictive actuator so as to calculate the frequency ratio FR1A, the frequency ratio FR1B, and the capacitance CP if necessary according to the present invention.

Figure 33A:
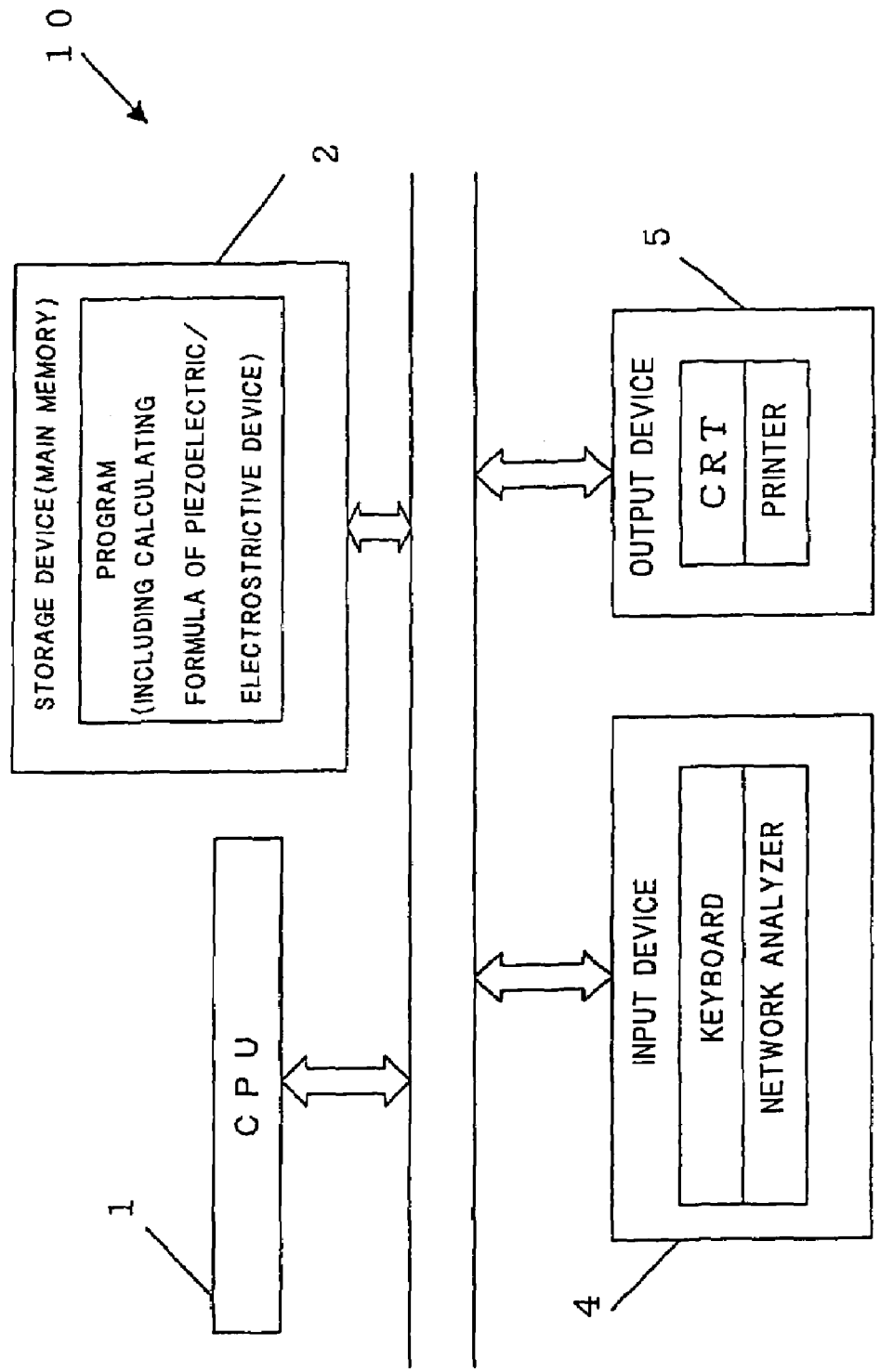
FIG. 33(a) is a diagram showing one example of a computer system including a prediction program of the amount of displacement of the piezoelectric/electrostrictive actuator according to the present invention.
Figure 33B:
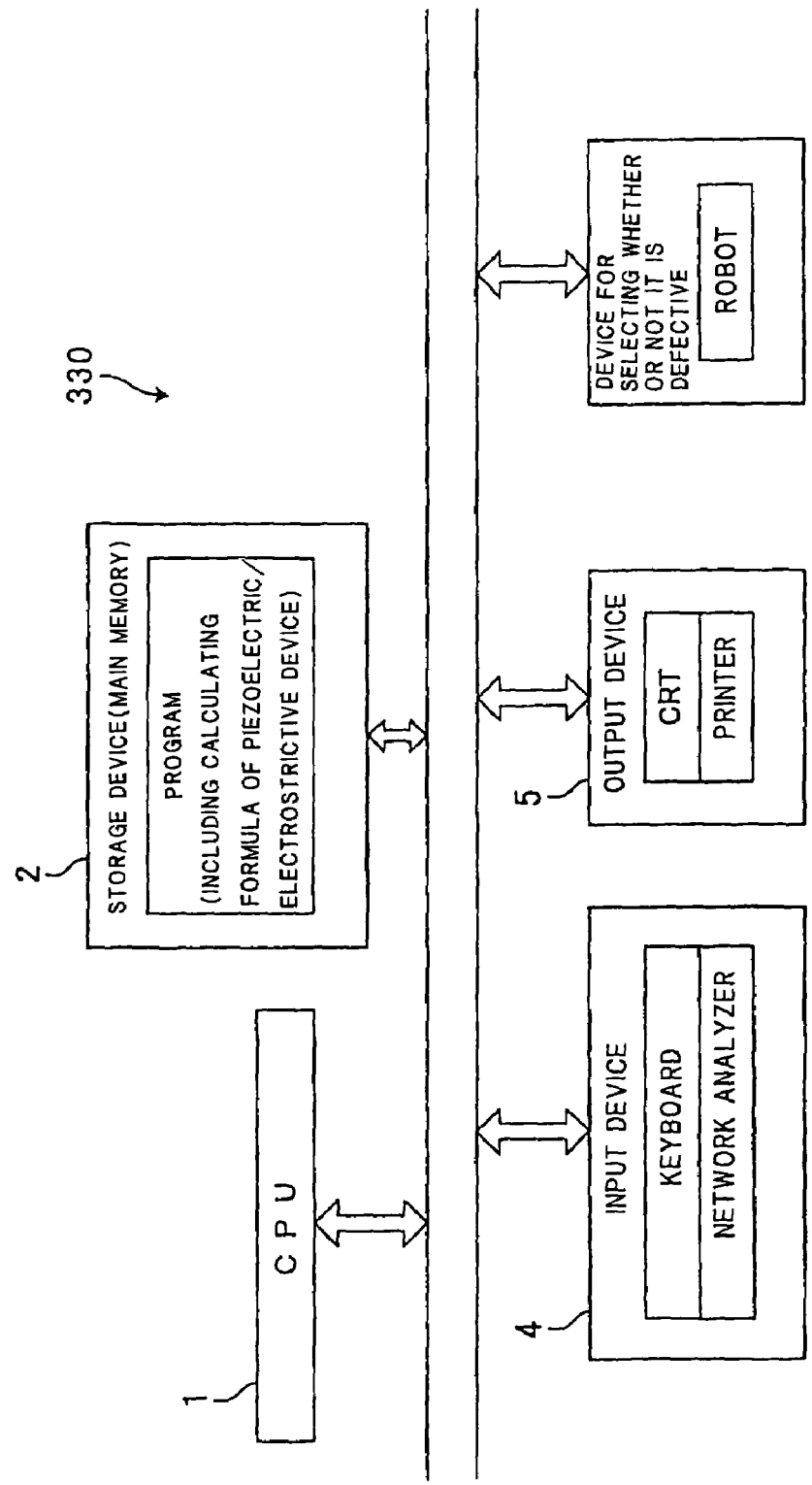
FIG. 33(b) is a diagram showing the structure of another example of the computer system including the prediction program of the amount of displacement of the piezoelectric/electrostrictive actuator according to the present invention.

Hereinbelow, a description is given of a prediction program of the amount of displacement of the piezoelectric/electrostrictive actuator (simply referred to as a prediction program of the amount of displacement). FIGS. 33(a) and 33(b) are diagrams showing the structure of a computer system including the prediction program of the amount of displacement. Referring to FIG. 33(a), a computer system 10 mainly comprises: a CPU (central processing unit) 1; a storage device 2 (main memory); an input device 4; and an output device 5. The prediction program of the amount of displacement according to the present invention enables a computer to function as predetermined means so as to predict the amount of displacement of the piezoelectric/electrostrictive actuator having the piezoelectric/electrostrictive element and two or more electrodes according to the present invention. The prediction program of the amount of displacement according to the present invention is stored in the storage device 2, and the CPU 1 issues instructions to another device forming the computer system 10 based on the prediction program of the amount of displacement.

The CPU 1 calculates the predicted amount of displacement of the piezoelectric/electrostrictive actuator based on the calculating formulae applied to the piezoelectric/electrostrictive actuator whose amount of displacement is predicted in response to the instructions of the prediction program of the amount of displacement. Subsequently, the CPU 1 outputs the obtained predicted amount of displacement of the piezoelectric/electrostrictive actuator to a printer or a CRT (screen) in response to the instructions of the prediction program of the amount of displacement. The calculating formulae can be incorporated in the prediction program of the amount of displacement. The calculating formulae are not limited those shown as examples, and can be changed in accordance with the property of an inspection target, such as an exponential function or a high-degree polynominal expression.

A description is given of the case of obtaining the predicted amount of displacement by using specific calculating formulae in the computer system 10. Inputted, via a keyboard or a network analyzer, is information including the resonant frequencies in the resonant modes of the first and high degrees, the peak height of the resonant waveform, and the area, upon vibrating the piezoelectric/electrostrictive actuator whose predicted amount of displacement is calculated. The CPU 1 calculates the ratio of resonant frequencies, the ratio of peak height and the ratio of areas, in response to the instructions of the prediction program of the amount of displacement in the storage device 2.

Further, the CPU 1 calculates the predicted amount of displacement of the piezoelectric/electrostrictive actuator based on [Formula 12] or [Formula 13], serving as calculating formulae for calculating the predicted amount of displacement of the piezoelectric/electrostrictive actuator, in response to the instructions of the amount of displacement in the storage device 2. In the case of using the capacitance to obtain the predicted amount of displacement (in [Formula 4], inputted, via a keyboard or an LCR meter, the capacitance CP of the piezoelectric/electrostrictive element of the piezoelectric/electrostrictive actuator whose predicted amount of displacement is calculated. The CPU 1 outputs the calculated predicted amount of displacement, serving as digital data or analog data, to a printer or a CRT (screen).

A computer system 330 shown in FIG. 33(b) additionally has a device (robot) for selecting whether or not a product is defective in addition to a computer system shown in FIG. 33(a). The predicted amount of displacement for each measured subject is stored in the storage device 2 based on information on the determination as whether or not the product is defective, and the information on the determination, based on a designated threshold, as whether or not the product is defective is stored in the storage device 2. The device (robot) for selecting whether or not the product is defective selects the subject (product of piezoelectric/electrostrictive actuator) based on the information on the determination as whether or not the product is defective, and a non-defective piezoelectric/electrostrictive actuator is placed on a tray for non-defective product, and a defective piezoelectric/electrostrictive actuator is placed on a tray for defective product.

The dimension predicting program of the elastic body according to the present invention enables a computer to function as predetermined means so as to predict the dimension (amount of deviation or amount of undulation) of the vibrating unit 66 in the base 44 or the piezoelectric/electrostrictive element 79 in the piezoelectric/electrostrictive operating unit 78, serving as an elastic body. The dimension predicting program according to the present invention is stored in the storage device 2 according to the prediction program of the amount of displacement, except for using [Formula 1] for calculating the predicted dimension, the CPU 1 issues instructions to another device forming the computer system 10 based on the dimension predicting program, and a detailed description thereof is omitted.

The description is given of the piezoelectric/electrostrictive actuator, serving as one example, in the inspecting method, the inspecting apparatus, and the prediction program of the amount of displacement of the piezoelectric/electrostrictive actuator according to the present invention. The piezoelectric/electrostrictive sensor in the inspecting method, the inspecting apparatus, and the prediction program of the amount of displacement of the piezoelectric/electrostrictive sensor is similar to the piezoelectric/electrostrictive actuator, serving as a structure, except for the differences of electrical/mechanical conversion and mechanical/electrical conversion.

According to the present invention, the piezoelectric/electrostrictive actuator in the inspecting method, the inspecting apparatus, and the prediction program of the amount of displacement of the piezoelectric/electrostrictive actuator comprises a piezoelectric/electrostrictive element, serving as an elastic body, and two or more electrodes, and therefore corresponds to a structure having two or more elastic bodies. In the specification, the piezoelectric/electrostrictive actuator comprises the piezoelectric/electrostrictive operating unit comprising the piezoelectric/electrostrictive element and two or more electrodes and the base, serving as an elastic body, comprising the vibrating unit and the supporting unit. In the example of the piezoelectric/electrostrictive actuator, the piezoelectric/electrostrictive operating unit, the vibrating unit, and the supporting unit are elastic bodies, respectively.

According to the present invention, the elastic body in the inspecting method, the inspecting apparatus, and the dimension predicting program of the elastic body is an object indicating not the plasticity but the elasticity, may be at least one of two or more elastic bodies forming the structure, and is not limited to the ceramic base (vibrating unit) and the piezoelectric/electrostrictive element (piezoelectric/electrostrictive operating unit).

According to the present invention, the piezoelectric/electrostrictive device in the inspecting method, the inspecting apparatus, and the prediction program of the amount of displacement of the piezoelectric/electrostrictive device and the piezoelectric/electrostrictive sensor in the inspecting method, the inspecting apparatus, and the prediction program of the detecting sensitivity of the piezoelectric/electrostrictive sensor are units having lump functions by using the charge/electric field induced by the strain or stress that is inducted by the electric field, comprise the piezoelectric/electrostrictive element and at least one pair of electrics, and are not limited to the piezoelectric/electrostrictive actuator using the inverse piezoelectric effect that generates the amount of strain proportional to the applied electric field, the piezoelectric effect that generates the amount of charges induced by the stress, and the piezoelectric/electrostrictive effect that generates the amount of strain proportional to the square of applied electric field, and include a piezoelectric/electrostrictive actuator using the phenomena, such as the reverse of polarization in the general ferroelectric material and the phase transition between the antiferroelectric phase and the ferroelectric phase in the general antiferroelectric material. Further, the polarization is appropriately determined depending on the nature of materials used for the piezoelectric/electrostrictive element forming the piezoelectric/electrostrictive actuator.

INDUSTRIAL APPLICABILITY

According to the present invention, preferably, the inspecting method, the inspecting apparatus, and the dimension predicting program of the elastic body according to the present invention and the inspecting method, the inspecting apparatus, and the prediction program of the amount of displacement of the piezoelectric/electrostrictive actuator can be applied as inspection means of various piezoelectric/electrostrictive actuators of a measurement instrument, an optical modulator, an optical switch, an electrical switch, a micro relay, a micro valve, a conveying device, and an image display device, such as a display or a projector, an image drawing device, a micro pump, a drop discharge device, a minute mixing device, a minute stirrer, and a minute reacting device. Further, preferably, the inspecting method, the inspecting apparatus, and the prediction program of the detecting sensitivity of the piezoelectric/electrostrictive sensor is used as inspection means of various piezoelectric/electrostrictive sensors used for detection of fluid property, sound pressure, minute weight, and acceleration.

What is claimed is:

1. An inspecting method of an elastic body in a structure having two or more elastic bodies, said method comprising:
   observing a frequency response characteristic of said two or more elastic bodies when a vibration is applied to said structure having two or more elastic bodies; and
   predicting a dimension of said two or more elastic bodies based on said frequency response characteristic;
   wherein said frequency response characteristic is one of the characteristics selected from the group consisting of a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies degrees.

2. An inspecting method of an elastic body according to claim 1, wherein said frequency response characteristic is one characteristic selected from the group consisting of a peak height PKx, an area Sx, and a difference between a maximum value and a minimum value of a resonance frequency of one degree, a ratio PKRxy of peak height, a difference PRDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

3. An inspecting method of a piezoelectric/electrostrictive actuator having a piezoelectric/electrostrictive element and two or more electrodes, said method comprising:
  observing a frequency response characteristic of said piezoelectric/electrostrictive actuator when a vibration is applied to said piezoelectric/electrostrictive actuator; and
  predicting an amount of displacement of said piezoelectric/electrostrictive actuator based on said frequency response characteristic;
  wherein said frequency response characteristic is a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies of other degrees.

4. An inspecting method of a piezoelectric/electrostrictive actuator according to claim 3, wherein said frequency response characteristic is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of other degrees and at least one of resonant frequencies of other degrees.

5. An inspecting method of a piezoelectric/electrostrictive sensor having a piezoelectric/electrostrictive element and two or more electrodes, said method comprising:
  observing a frequency response characteristic of said piezoelectric/electrostrictive sensor when a vibration is applied to said piezoelectric/electrostrictive sensor; and
  predicting a detecting sensitivity of said piezoelectric/electrostrictive sensor based on said frequency response characteristic;
  wherein said frequency response characteristic is a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies of other degrees.

6. An inspecting method of a piezoelectric/electrostrictive sensor according to claim 5, wherein said frequency response characteristic is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

7. An inspecting apparatus of an elastic body in a structure having two or more elastic bodies, said apparatus comprising:
  means for observing a frequency response characteristic of said two or more elastic bodies when a vibration is applied to said structure having said two or more elastic bodies; and
  means for predicting a dimension of said two or more elastic bodies based on said frequency response characteristic;
  wherein said frequency response characteristic is a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies of other degrees.

8. An inspecting apparatus of an elastic body according to claim 7, wherein said frequency response characteristic is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and resonant frequencies of other degrees.

9. An inspecting apparatus of a piezoelectric/electrostrictive actuator having a piezoelectric/electrostrictive element and two or more electrodes, said apparatus comprising:
  means for observing a frequency response characteristic of said piezoelectric/electrostrictive actuator when a vibration is applied to said piezoelectric/electrostrictive actuator; and
  means for predicting an amount of displacement of said piezoelectric/electrostrictive actuator based on said frequency response characteristic;
  wherein said frequency response characteristic is a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies of other degrees.

10. An inspecting apparatus of a piezoelectric/electrostrictive actuator according to claim 9, wherein said frequency response characteristic is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

11. An inspecting apparatus of a piezoelectric/electrostrictive sensor having a piezoelectric/electrostrictive element and two or more electrodes, said apparatus comprising:
  means for observing a frequency response characteristic of said piezoelectric/electrostrictive sensor when a vibration is applied to said piezoelectric/electrostrictive sensor; and
  means for predicting a detecting sensitivity of said piezoelectric/electrostrictive sensor based on said frequency response characteristic;
  wherein said frequency response characteristic is a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies of other degrees.

12. An inspecting apparatus of a piezoelectric/electrostrictive sensor having a piezoelectric/electrostrictive element and two or more electrodes, said apparatus comprising:
  means for observing a frequency response characteristic of said piezoelectric/electrostrictive sensor when a vibration is applied to said piezoelectric/electrostrictive sensor; and
  means for predicting a detecting sensitivity of said piezoelectric/electrostrictive sensor based on said frequency response characteristic;
  wherein said frequency response characteristic is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

13. A dimension predicting program, for predicting a dimension of an elastic body in a structure having two or more of elastic bodies, provided on a computer readable medium to enable a computer to function as:
  means for inputting a measurement value of a frequency response characteristic of a structure having two or more of elastic bodies whose predicted dimension is calculated;
  means for obtaining a predicted dimension of said elastic body of said structure based on a calculating formula of the predicted dimension; and
  means for outputting thus obtained predicted dimension of said elastic body of said structure to one of a CRT, printer, and a selector device that uses the obtained data to determine whether the structure is defective and selects defective structures for removal.

14. A prediction program, for predicting an amount of displacement of a piezoelectric/electrostrictive actuator for predicting an amount of displacement of said piezoelectric/electrostrictive actuator having a piezoelectric/electrostrictive element and two or more electrodes, provided on a computer readable medium to enable a computer to function as:
  means for inputting a frequency response characteristic of said piezoelectric/electrostrictive actuator whose predicted amount of displacement is calculated;
  means for obtaining a predicted amount of displacement of said piezoelectric/electrostrictive actuator based on a calculating formula of the predicted amount of displacement; and
  means for outputting thus obtained predicted amount of displacement of said piezoelectric/electrostrictive actuator to one of a CRT, printer, and a selector device that uses the obtained data to determine whether the structure is defective and selects defective structures for removal.

15. A prediction program, for predicting a detecting sensitivity of a piezoelectric/electrostrictive sensor, provided on a computer readable medium to enable a computer to function as:
  means for inputting a frequency response characteristic of a piezoelectric/electrostrictive sensor whose predicted detecting sensitivity is to be calculated;
  means for obtaining a predicted detecting sensitivity of said piezoelectric/electrostrictive sensor based on a calculating formula of said detecting sensitivity; and
  means for outputting thus obtained predicted detecting sensitivity of said piezoelectric/electrostrictive sensor to one of a CRT, printer, and a selector device that uses the obtained data to determine whether the structure is defective and selects defective structures for removal.

16. An inspecting method of an elastic body in a structure having two or more elastic bodies, said method comprising:
  observing a frequency response characteristic of said two or more elastic bodies of said structure when a vibration is applied to said structure; and
  predicting a dimension of said two or more elastic bodies of said structure based on said observed frequency characteristic of said two or more elastic bodies of said structure using data representing a relationship between a frequency response characteristic of a standard body having at least one known dimension and said dimension of said standard body as a vibration is applied thereto;
  wherein said frequency response characteristic is one of the characteristics selected from the group consisting of a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies degrees.

17. An inspecting method of an elastic body in a structure having two or more elastic bodies, said method comprising:
  observing a frequency response characteristic of said two or more elastic bodies of said structure when a vibration is applied to said structure; and
  predicting a dimension of said two or more elastic bodies of said structure based on said observed frequency characteristic of said two or more elastic bodies of said structure using data representing a relationship between a frequency response characteristic of a standard body having at least one known dimension and said dimension of said standard body as a vibration is applied thereto;

wherein said frequency response characteristic is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

18. An inspecting apparatus of an elastic body in a structure having two or more elastic bodies, said apparatus comprising:

means for observing a frequency response characteristic of said two or more elastic bodies of said structure when a vibration is applied to said structure; and means for predicting a dimension of said two or more elastic bodies of said structure based on said observed frequency response characteristic of said two or more elastic bodies of said structure using data representing a relationship between an observed frequency response characteristic of a standard elastic body having at least one known dimension and said dimension of said standard body as a vibration is applied thereto;

wherein said frequency response characteristic is one of the characteristics selected from the group consisting of a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies degrees.

19. An inspecting apparatus of an elastic body in a structure having two or more elastic bodies, said apparatus comprising:

means for observing a frequency response characteristic of said two or more elastic bodies of said structure when a vibration is applied to said structure; and means for predicting a dimension of said two or more elastic bodies of said structure based on said observed frequency response characteristic of said two or more elastic bodies of said structure using data representing a relationship between an observed frequency response characteristic of a standard elastic body having at least one known dimension and said dimension of said standard body as a vibration is applied thereto;

wherein said frequency response characteristic is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

20. An inspecting method of a piezoelectric/electrostrictive actuator having a piezoelectric/electrostrictive element and two or more electrodes, said method comprising:

observing a frequency response characteristic of said piezoelectric/electrostrictive actuator as a vibration is applied to said piezoelectric/electrostrictive actuator; and predicting an amount of displacement of said piezoelectric/electrostrictive actuator based on said observed frequency response characteristics of said piezoelectric/electrostrictive actuator using data representing a relationship between an observed frequency characteristic of a standard body having at least one known dimension and said dimension of said standard body when a vibration is applied thereto;

wherein said frequency response characteristic is one of the characteristics selected from the group consisting of a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies degrees.

21. An inspecting method of a piezoelectric/electrostrictive actuator having a piezoelectric/electrostrictive element and two or more electrodes, said method comprising:

observing a frequency response characteristic of said piezoelectric/electrostrictive actuator as a vibration is applied to said piezoelectric/electrostrictive actuator; and predicting an amount of displacement of said piezoelectric/electrostrictive actuator based on said observed frequency response characteristics of said piezoelectric/electrostrictive actuator using data representing a relationship between an observed frequency characteristic of a standard body having at least one known dimension and said dimension of said standard body when a vibration is applied thereto;

wherein said frequency response characteristic is one characteristic selected from the group consisting of a peak height PKx, an area Sx, and a difference between a maximum value and a minimum value of a resonance frequency of one degree, a ratio PKLRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

22. An inspecting apparatus of a piezoelectric/electrostrictive actuator having a piezoelectric/electrostrictive element and two or more electrodes, said apparatus comprising:

means for observing a frequency response characteristic of said piezoelectric/electrostrictive actuator when a vibration is applied to said piezoelectric/electrostrictive actuator; and means for predicting an amount of displacement of said piezoelectric/electrostrictive actuator based on said observed frequency response characteristic of said piezoelectric/electrostrictive actuator using data representing a relationship between an observed frequency response characteristic of a standard body having at least one known dimension and said dimension of said standard body as a vibration is applied to the standard body;

wherein said frequency response characteristic is one of the characteristics selected from the group consisting of a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies degrees.

23. An inspecting apparatus of a piezoelectric/electrostrictive actuator having a piezoelectric/electrostrictive element and two or more electrodes, said apparatus comprising:

means for observing a frequency response characteristic of said piezoelectric/electrostrictive actuator when a vibration is applied to said piezoelectric/electrostrictive actuator; and means for predicting an amount of displacement of said piezoelectric/electrostrictive actuator based on said observed frequency response characteristic of said piezoelectric/electrostrictive actuator using data representing a relationship between an observed frequency response characteristic of a standard body having at least one known dimension and said dimension of said standard body as a vibration is applied to the standard body;

wherein said frequency response characteristic is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

24. An inspecting method of a piezoelectric/electrostrictive sensor having a piezoelectric/electrostrictive element and two or more electrodes, said method comprising:

observing a frequency response characteristic of said piezoelectric/electrostrictive sensor when a vibration is applied to said piezoelectric/electrostrictive sensor; and predicting a detection sensitivity of said piezoelectric/electrostrictive sensor based on said observed frequency response characteristic of said piezoelectric/electrostrictive sensor using data representing a relationship between an observed frequency characteristic of a standard body having at least one known dimension and said dimension of said standard body when a vibration is applied thereto;

wherein said frequency response characteristic is one of the characteristics selected from the group consisting of a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies degrees.

25. An inspecting method of a piezoelectric/electrostrictive sensor having a piezoelectric/electrostrictive element and two or more electrodes, said method comprising:

observing a frequency response characteristic of said piezoelectric/electrostrictive sensor when a vibration is applied to said piezoelectric/electrostrictive sensor; and predicting a detection sensitivity of said piezoelectric/electrostrictive sensor based on said observed frequency response characteristic of said piezoelectric/electrostrictive sensor using data representing a relationship between an observed frequency characteristic of a standard body having at least one known dimension and said dimension of said standard body when a vibration is applied thereto;

wherein said frequency response characteristic is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

26. An inspecting apparatus of a piezoelectric/electrostrictive sensor having a piezoelectric/electrostrictive element and two or more electrodes, said apparatus comprising:

means for observing a frequency response characteristic of said piezoelectric/electrostrictive sensor when a vibration is applied to said piezoelectric/electrostrictive sensor; and means for predicting a detecting sensitivity of said piezoelectric/electrostrictive sensor based on said observed frequency characteristic of said piezoelectric/electrostrictive sensor using data representing a relationship between an observed frequency characteristic of a standard body having at least one known dimension and said dimension of said standard body when a vibration is applied thereto;

wherein said frequency response characteristic is one of the characteristics selected from the group consisting of a combination of a resonance frequency Fx of one degree and at least one of resonant frequencies Fy of other degrees, one or more of frequency ratios FRxy wherein FRxy is Fy/Fx obtained by using said resonance frequency Fx of one degree and said at least one of resonant frequencies of other degrees and one or more of frequency differences FDxy (wherein FDxy is Fy-Fx) obtained by using said resonance frequency Fx of one degree and said at least one of resonant frequencies degrees.

27. An inspecting apparatus of a piezoelectric/electrostrictive sensor having a piezoelectric/electrostrictive element and two or more electrodes, said apparatus comprising:

means for observing a frequency response characteristic of said piezoelectric/electrostrictive sensor when a vibration is applied to said piezoelectric/electrostrictive sensor; and means for predicting a detecting sensitivity of said piezoelectric/electrostrictive sensor based on said observed frequency characteristic of said piezoelectric/electrostrictive sensor using data representing a relationship between an observed frequency characteristic of a standard body having at least one known dimension and said dimension of said standard body when a vibration is applied thereto;

wherein said frequency response characteristic is one characteristic selected from the group consisting of a peak height PKx, an area Sx, and a difference between a maximum value and a minimum value of a resonance frequency of one degree, a ratio PKRxy of peak height, a difference PKDxy of peak height an area ratio SRxy, an area difference SDxy, a ratio of the difference between the maximum value and the minimum value, and a difference of the differences between the maximum value and the minimum value between said resonance frequency of one degree and at least one of resonant frequencies of other degrees.

* * * * *

UNITED STATES PATENT AND TRADEMARK OFFICE
CERTIFICATE OF CORRECTION

| | |
|---|---|
| PATENT NO. | : 7,424,827 B2 |
| APPLICATION NO. | : 11/115981 |
| DATED | : September 16, 2008 |
| INVENTOR(S) | : Tomohiro Yamada et al. |

Page 1 of 1

It is certified that error appears in the above-identified patent and that said Letters Patent is hereby corrected as shown below:

Column 33

*Line 4*: please change "PRDxy" to --PKDxy--

*Line 44*: please change "PKLRxy" to --PKRxy--

Signed and Sealed this

Sixteenth Day of December, 2008

JON W. DUDAS
*Director of the United States Patent and Trademark Office*